(12) United States Patent
Espinoza et al.

(10) Patent No.: US 11,857,557 B2
(45) Date of Patent: Jan. 2, 2024

(54) ORAL DISSOLVABLE FILM CONTAINING VITAMIN D3

(71) Applicant: CURE Pharmaceutical, Inc., Oxnard, CA (US)

(72) Inventors: Maribel Espinoza, Oxnard, CA (US); Jose Bernardo, Oxnard, CA (US)

( * ) Notice: Subject to any disclaimer, the term of this patent is extended or adjusted under 35 U.S.C. 154(b) by 296 days.

(21) Appl. No.: 17/038,494

(22) Filed: Sep. 30, 2020

(65) Prior Publication Data

US 2021/0145849 A1    May 20, 2021

Related U.S. Application Data

(60) Provisional application No. 62/907,855, filed on Sep. 30, 2019.

(51) Int. Cl.
| | |
|---|---|
| *A61K 31/593* | (2006.01) |
| *A61K 9/00* | (2006.01) |
| *A61K 47/38* | (2006.01) |
| *A61K 47/26* | (2006.01) |
| *A61K 47/44* | (2017.01) |
| *A61K 47/10* | (2017.01) |
| *A61K 47/22* | (2006.01) |
| *A61K 47/32* | (2006.01) |

(52) U.S. Cl.
CPC .......... *A61K 31/593* (2013.01); *A61K 9/0056* (2013.01); *A61K 47/10* (2013.01); *A61K 47/22* (2013.01); *A61K 47/26* (2013.01); *A61K 47/32* (2013.01); *A61K 47/38* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 6,495,177 B1 | 12/2002 | deVries et al. | |
| 7,850,987 B2 | 12/2010 | Moneymaker et al. | |
| 9,023,382 B2 * | 5/2015 | Ali | A61P 29/00 424/443 |
| 9,901,545 B1 * | 2/2018 | Fuisz | A61K 9/0056 |
| 10,130,641 B2 | 11/2018 | Howe et al. | |
| 2005/0226906 A1 | 10/2005 | Moneymaker et al. | |
| 2005/0226907 A1 | 10/2005 | Moneymaker et al. | |
| 2007/0087036 A1 | 4/2007 | Durschlag et al. | |
| 2008/0193602 A1 | 8/2008 | Moneymaker et al. | |
| 2010/0047223 A1 | 2/2010 | Moneymaker et al. | |
| 2010/0234329 A1 | 9/2010 | Bélanger et al. | |
| 2011/0123507 A1 | 5/2011 | Moneymaker et al. | |
| 2014/0335153 A1 * | 11/2014 | Allen | A61K 9/006 514/474 |
| 2017/0202860 A1 | 7/2017 | Howe et al. | |
| 2017/0290870 A1 * | 10/2017 | Schaneville | A61K 47/26 |
| 2018/0104183 A1 | 4/2018 | Kawamura et al. | |
| 2019/0021385 A1 | 1/2019 | Fernandez | |
| 2019/0083514 A1 | 3/2019 | Howe et al. | |
| 2019/0336453 A1 | 11/2019 | Kataria et al. | |

FOREIGN PATENT DOCUMENTS

| | | |
|---|---|---|
| EP | 1740159 A1 | 1/2007 |
| EP | 3565532 A1 | 11/2019 |
| EP | 3281625 A1 | 2/2020 |
| WO | 2001011991 A1 | 2/2001 |
| WO | 2005097085 A1 | 10/2005 |
| WO | 2005102295 A1 | 11/2005 |
| WO | 2006119286 A1 | 11/2006 |
| WO | 2009048270 A1 | 4/2009 |
| WO | 2009055923 A1 | 5/2009 |
| WO | 2016163403 A1 | 10/2016 |
| WO | 2018127938 A1 | 7/2018 |

OTHER PUBLICATIONS

Umang (Vitamin D3 oral thin mouth dissolving film, available online Jun. 26, 2017, via Way Back Machine Archive). (Year: 2017).*

* cited by examiner

*Primary Examiner* — Melissa S Mercier
(74) *Attorney, Agent, or Firm* — Carlson, Caspers, Vandenburgh & Lindquist, P.A.

(57) ABSTRACT

The present invention relates to an oral dissolvable film (ODF) containing an active ingredient (e.g., vitamin D) that is, outside of the ODF, relatively unstable to at least one of heat, light, moisture, and oxygen. The present invention also relates to methods of manufacturing and using the same.

26 Claims, No Drawings

ORAL DISSOLVABLE FILM CONTAINING VITAMIN D3

RELATED APPLICATION

This U.S. utility patent application claims priority from U.S. Provisional Patent Application Ser. No. 62/907,855, filed Sep. 30, 2019, the contents of which are incorporated by reference herein it its entirety.

TECHNICAL FIELD

The present invention relates to an oral dissolvable film (ODF) containing an active ingredient (e.g., vitamin $D_3$) that is, outside of the ODF, relatively unstable to at least one of heat, light, moisture, and oxygen.

BACKGROUND OF THE INVENTION

An oral dissolvable film (ODF) is a dosage form that uses a dissolving film or strip to administer drugs via absorption in the mouth (buccally or sublingually) and/or via the small intestines (enterically). A film is typically prepared using hydrophilic polymers that rapidly dissolve on the tongue or buccal cavity, delivering the drug to the systemic circulation via dissolution when contact with liquid (saliva) is made.

ODF drug delivery has emerged as an advanced alternative dosage form to the traditional tablets, capsules and liquids often associated with prescription and over-the-counter (OTC) medications, as well as nutraceuticals. Similar in size, shape and thickness to a postage stamp, ODF strips are designed for oral administration, with the user placing the strip on or under the tongue (sublingual) or along the inside of the cheek (buccal). These drug delivery options allow the medication to bypass the first pass metabolism thereby making the medication more bioavailable. As the strip dissolves, the drug can enter the blood stream enterically, buccally or sublingually.

Oral dissolvable films are becoming an increasingly popular dosage form for the oral administration of active ingredients. The use of ODFs can eliminate some common problems associated with oral solid-dosage forms (e.g., tablets and capsules), such as the fear or risk of choking associated with swallowing an oral solid-dosage forms, ease of transportation, difficulty in swallowing (dysphagia), the need for water intake with an oral solid-dosage forms, and/or the ability to be discrete when taking the medication.

ODFs can therefore be used for achieving clinical benefits, such as enhancing oral absorption and bioavailability and improving patient compliance. ODFs can therefore offer significant benefits to patient populations such as, e.g., geriatric and pediatric patients, as well as those suffering from a psychological, degenerative and/or neurological disorder, and those who are bedridden, emetic patients, those suffering from diarrhea, those suffering from sudden episode of allergic attacks, or coughing, and those who have an active life style. They also offer significant benefits to those patients wanting to administer the medication in a discreet, inconspicuous, unnoticeable and/or private manner, especially while in the company of another. ODFs can therefore be administered without the use of water, fulfilling the need of target population seeking convenience in drug administration, along with rapid onset of action with increased bioavailability due to bypassing the first pass metabolism, consequently, leading to improved therapeutic response.

Just as with other dosage forms intended for oral administration, ODFs have typically been limited for use with specific active ingredients (e.g., those that are not sensitive to at least one of heat, light, moisture, and oxygen). What is needed, therefore, is an oral dissolvable film that can include additional classes of active ingredient (e.g., heat sensitive, light sensitive, moisture sensitive, oxygen sensitive, etc.) not present in commercially manufactured ODFs, while maintaining the target aesthetics and performance characteristics of the ODF (e.g., desired content uniformity, desired thickness, and/or desired dissolution/disintegration).

SUMMARY OF THE INVENTION

The present invention overcomes disadvantages of the prior art by providing an oral dissolvable film (ODF) containing an active ingredient (e.g., vitamin $D_3$) that is, outside of the ODF, relatively unstable to at least one of heat, light, moisture, and oxygen. With the active ingredient vitamin $D_3$ specifically, the ODF is administered to a subject in need thereof, e.g., for treating vitamin D deficiency in a human afflicted with vitamin D deficiency. Further, the vitamin $D_3$ ODF contains a therapeutically effective amount of the vitamin $D_3$ (e.g., up to 50,000±10,000 IU per oral dissolvable film) while possessing a requisite thickness (e.g., about 0.130±0.004 mm), mass (e.g., less than 100 mg), and water content (e.g., 10±5 wt. %) to effectively disintegrate, within the desired period of time (e.g., up to 30 seconds), when placed in the oral cavity. The vitamin $D_3$ ODF has a suitable average pH (e.g., 7.0±0.1) and tensile strength (e.g., 16.5±1.9 Newtons). The vitamin $D_3$ ODF is formulated and manufactured to maintain both the stability and the content uniformity of the vitamin $D_3$, when present within the ODF. These are maintained over the extended periods of time typically encountered with the shipment and storage of the commercial drug product. When the vitamin $D_3$ ODF is administered orally, the vitamin $D_3$ is delivered either enterally (the ODF is placed on the top of the tongue), sublingually (the ODF is placed under the tongue), or transmucosally (the ODF is placed against the cheek). The vitamin $D_3$ ODF was also found to surprisingly have suitable organoleptic properties. While the vitamin $D_3$ ODF in specific embodiments is formulated for 1 ODF administered once per week, a variety of dosing regimens (e.g., 1-3 ODFs administered as needed, 1-3 ODFs administered once daily, 1-3 ODFs administered once weekly, 1-3 ODFs administered once every two weeks, etc.) can be targeted.

The present invention provides an oral dissolvable film that includes: (a) a polymeric matrix; (b) an active ingredient; (c) an antioxidant; and (d) optionally at least one of a sweetener, flavoring agent, and coloring agent.

The present invention also provides an oral dissolvable film that includes (a)-(d): (a) a polymeric matrix that includes (i)-(iv): (i) a binder; (ii) a thickening agent; (iii) a plasticizer; and (iv) an emulsifier; (b) an active ingredient; (c) an antioxidant; and (d) optionally at least one of a sweetener, flavoring agent, and coloring agent.

The present invention also provides an oral dissolvable film that includes (i)-(xii): (i) solvent, (ii) binder, (iii) thickening agent, (iv) solubilizer, (v) plasticizer, (vi) emulsifier, (vii) filler, (viii) antioxidant, (ix) active ingredient, (x) optionally flavoring agent, (xi) optionally sweetener, and (xii) optionally coloring agent.

The present invention also provides an oral dissolvable film that includes (i)-(xii): (i) solvent, (ii) binder, (iii) thickening agent, (iv) solubilizer, (v) plasticizer, (vi) emulsifier, (vii) filler, (viii) antioxidant, (ix) cholecalciferol (vitamin $D_3$), (x) flavoring agent, (xi) sweetener, and (xii) coloring agent.

The present invention also provides an oral dissolvable film that includes (a)-(g): (a) a binder selected from the group consisting of carboxymethyl cellulose sodium, sodium alginate, and combinations thereof; (b) a thickening agent selected from the group consisting of polyvinylpyrrolidone, hydroxypropyl methyl cellulose, and combinations thereof; (c) a plasticizer that includes glycerin; (d) an emulsifier that includes polysorbate 80; (e) an active ingredient; (f) an antioxidant; and (g) optionally at least one of a sweetener, flavoring agent, and coloring agent.

The present invention also provides an oral dissolvable film that includes (a)-(j): (a) sodium carboxymethylcellulose; (b) polyvinylpyrrolidone; (c) cocoa butter; (d) glycerin; (e) polysorbate 80; (f) microcrystalline cellulose; (g) at least one of tocopheryl acetate (vitamin E acetate), ascorbyl palmitate, vitamin E, and butylated hydroxytoluene (BHT); (h) cholecalciferol (vitamin $D_3$); (i) flavoring agent; and (j) sweetener.

The present invention also provides an oral dissolvable film that includes (a)-(k): (a) 19.19±3 wt. % sodium carboxymethyl cellulose (Na CMC); (b) 11.71±2 wt. % Kollidon® 90 F (polyvinylpyrrolidone); (c) 4.53±1 wt. % cocoa butter; (d) 9.16±1.5 wt. % glycerin; (e) 7.32±1 wt. % polysorbate 80; (f) 9.27±0.25 wt. % Endurance™ microcrystalline cellulose (MCC); (g) 9.25±1.25 wt. % in the aggregate of ascorbyl palmitate, butylated hydroxytoluene (BHT), tocopheryl acetate (vitamin E acetate), vitamin E, or a combination thereof; (h) 1.95±0.5 wt. % cholecalciferol (vitamin $D_3$); (i) 17.27±2 wt. % flavoring agent; (j) 2.33±0.25 wt. % sweetener; and (k) 8.0±5 wt. % water.

The present invention also provides an oral dissolvable film that includes

| Ingredient | Amount (wt. %) in hydrous strip |
|---|---|
| Water (solvent) | 8.00 ± 3 wt. % |
| Sodium Carboxymethyl Cellulose (binder) | 19.19 ± 2 wt % |
| Kollidon ® 90 F PVP (thickening agent) | 11.71 ± 1 wt. % |
| Natural Deodorized Cocoa Butter (solubilizer) | 4.53 ± 0.5 wt. % |
| Glycerin 99.7% USP (plasticizer) | 9.16 ± 1.5 wt. % |
| Polysorbate 80, NF (emulsifier) | 7.32 ± 1 wt. % |
| Mountain Berry (flavor) | 9.61 ± 1.5 wt. % |
| Sucralose USP/NF (sweetener) | 2.33 ± 0.5 wt. % |
| Endurance ™ Microcrystalline Cellulose, (MCC) (filler) | 9.27 ± 1.5 wt. % |
| Vitamin E Oil 1000 IU (antioxidant) | 9.20 ± 1.5 wt. % |
| Ascorbyl Palmitate (antioxidant) | 0.05 ± 0.01 wt. % |
| Vitamin D3 (active) | 1.95 ± 0.3 wt. % |
| Nat & Art Mixed Berry (flavor) | 7.66 ± 0.7 wt. % |
| FD&C Red #40 (coloring agent) | 0.01 ± 0.001 wt. % |
| Total | 100.00 wt. % |

The present invention also provides an oral dissolvable film that includes

| Ingredient | Amount (wt. %) in hydrous strip |
|---|---|
| Water (solvent) | 8.00 wt. % |
| Sodium Carboxymethyl Cellulose (binder) | 19.19 wt. % |
| Kollidon ® 90 F PVP (thickening agent) | 11.71 wt. % |
| Natural Deodorized Cocoa Butter (solubilizer) | 4.53 wt. % |
| Glycerin 99.7% USP (plasticizer) | 9.16 wt. % |
| Polysorbate 80, NF (emulsifier) | 7.32 wt. % |
| Mountain Berry (flavor) | 9.61 wt. % |
| Sucralose USP/NF (sweetener) | 2.33 wt. % |
| Endurance ™ Microcrystalline Cellulose, (MCC) (filler) | 9.27 wt. % |
| Vitamin E Oil 1000 IU (antioxidant) | 9.20 wt. % |
| Ascorbyl Palmitate (antioxidant) | 0.05 wt. % |
| Vitamin D3 (active) | 1.95 wt. % |
| Nat & Art Mixed Berry (flavor) | 7.66 wt. % |
| FD&C Red #40 (coloring agent) | 0.01 wt. % |
| Total | 100.00 wt. % |

The present invention also provides a method of delivering an active ingredient to a subject in need thereof. The method includes orally administering to the subject an oral dissolvable film described herein.

The present invention also provides a method of delivering an active ingredient to a subject in need thereof. The method includes orally administering to the subject an oral dissolvable film described herein, wherein the active ingredient includes cholecalciferol (vitamin $D_3$), present in 50K±10K IU, and wherein the administration occurs once weekly.

The present invention also provides a method of delivering an active ingredient to a subject in need thereof. The method includes orally administering to the subject an oral dissolvable film described herein, wherein the active ingredient includes cholecalciferol (vitamin $D_3$), present in 40K±10K IU, and wherein the administration occurs once weekly.

DETAILED DESCRIPTION OF THE INVENTION

As used herein, the following terms have the meanings ascribed to them unless specified otherwise.

Definitions

The term "moisture sensitive active ingredient" refers to an active ingredient that will react with water or moisture, under normal ambient conditions (e.g., at about 20 C). The moisture sensitive active ingredient can degrade when directly contacting water or moisture. Thus, moisture-sensitive active ingredients often are not formulated to be in direct contact with water during the manufacturing of the dosage form. This holds true as well with any direct contact with water or moisture during the extended periods of time associated with the storage and shipment of the dosage form.

The term "oxygen sensitive active ingredient" refers to an active ingredient that will react with oxygen, under normal ambient conditions (e.g., at about 20 C). The oxygen sensitive active ingredient can degrade when directly contacting oxygen. Thus, oxygen-sensitive active ingredients often are not formulated to be in direct contact with oxygen during the extended periods of time associated with the storage and shipment of the dosage form.

The term "heat sensitive active ingredient" refers to an active ingredient susceptible to degradation at elevated temperatures (e.g., at or above about 40 C). Thus, heat-sensitive active ingredients often are not formulated at elevated temperatures during the manufacturing of the dosage form. This holds true as well with any elevated temperatures during the extended periods of time associated with the storage and shipment of the dosage form.

The term "light (UV) sensitive active ingredient" refers to an active ingredient susceptible to degradation upon extended exposure to light (UV), under normal ambient conditions (e.g., at about 20° C.). Thus, light-sensitive active ingredients often are not formulated to be in direct contact with light (UV) (at least not extended exposures) during the manufacturing of the dosage form. This holds true as well with any direct exposure to light (UV) during the extended periods of time associated with the storage and shipment of the dosage form.

The term "film" refers to a flexible polymeric matrix, composed of pharmaceutical or food grade ingredients, relatively flat and having a discrete dimension. Preferably, the film will also be self-supporting or in other words be able to maintain their integrity and structure in the absence of a separate support. The film can exist in either the unwound form (e.g., sheet) or in the wound form (e.g., bulk roll). The film is specifically configured for use with mucosal surfaces (e.g., oral, vaginal, nasal, etc.).

The term "oral dissolvable film," "oral soluble film," or "oral film" refers to a film, as described herein, that is specifically configured for oral administration. Oral dissolvable films are composed of pharmaceutically acceptable ingredients that are edible or ingestible. The oral film can be configured for multi- or unidirectional release.

The term "pharmaceutically acceptable" refers to a substance (e.g., excipient) being approved by a governmental regulatory agency, including being listed in the US FDA's Inactive Ingredient Database (IID), the US pharmacopoeia, or another generally recognized pharmacopoeia for use in animals, and more particularly in humans. Encompassed within the meaning of "pharmaceutically acceptable" is "food grade" and/or "food safe," e.g., for nutraceutical products.

The term "flowable" refers to a substance (e.g., oral dissolvable film or slurry) capable of flowing or being flowed.

The term "water-soluble" refers to a substance (e.g., oral dissolvable film) capable of dissolving in water. This includes at least 1 mg of the substance completely dissolving in up to 100 ml water in up to 10 minutes with agitation at ambient conditions (e.g., 20° C. and 50% RH).

The term "water swellable" refers to a substance (e.g., oral dissolvable film) capable of swelling or expanding in water. This includes the substance having an increase in volume of at least 5% upon being immersed in water at 20° C.

The term "film-forming" refers to a substance (e.g., slurry) capable of forming a film (e.g., oral dissolvable film) on a solid substrate. This includes curing the substance at elevated temperatures, as well as room temperature.

The term "matrix" or "film matrix" or "polymeric matrix" refers to an environment of substances in which a unit dosage form (e.g., an oral dissolvable film) is formed. This includes, e.g., a solvent, binder, thickening agent, plasticizer, and emulsifier to form a slurry (which can further include an active ingredient, antioxidant, and optionally additional substances such as, e.g., sweetener, flavoring agent, coloring agent, binder, thickening agent, plasticizer, emulsifier, solubilizer, and filler), which is subsequently cured to form an oral dissolvable film.

The term "active ingredient" or "active pharmaceutical ingredient" or "API" is used to include any "drug," "bioactive agent," "preparation," "medicament," "therapeutic agent," "physiological agent," "nutraceutical," or "pharmaceutical agent" and includes substances for use in the treatment of a disease or disorder. Dietary supplements, vitamins (e.g., vitamin $D_3$), functional foods (e.g., ginger, green tea, lutein, garlic, lycopene, capsaicin, and the like) are also included in this term. The term "active ingredient" also includes bioactive cannabinoids (e.g., CBD and THC) as well as terpenes (beta caryophyllene).

The term "active ingredient (e.g., vitamin $D_3$)" being "outside of the ODF" and "relatively unstable to at least one of heat, light, moisture, and oxygen" refers to the active ingredient as it typically exists as a drug substance. In such a form, the active ingredient is relatively unstable to at least one of heat, light, moisture, and oxygen. This is not intended to state, or suggest, that the active ingredient within the ODF is necessarily stable, per se, to heat, light, moisture, and/or oxygen. That said, it is believed that the active ingredient within the ODF (compared to the active ingredient as a drug substance) will have an increased stability to heat, light, moisture, and/or oxygen.

The term "vitamin D" a group of fat-soluble secosteroids responsible for increasing intestinal absorption of calcium, magnesium, and phosphate, and multiple other biological effects. Several forms (vitamers) of vitamin D exist. In humans, the most important compounds in this group are vitamin D3 (also known as cholecalciferol) and vitamin D2 (ergocalciferol). These are known collectively as calciferol.

The term "vitamin D3" or "vitamin $D_3$," or "cholecalciferol" or "activated 7-dehydrocholesterol" refers to a type of vitamin D which is made by the skin when exposed to sunlight. The IUPAC name is (3S,5Z,7E)-9,10-secocholesta-5,7,10(19)-trien-3-ol; the molecular formula is $C_{27}H_{44}O$; and the molar mass is 384.64 g/mol. When present in the oral dissolvable film described herein, the vitamin $D_3$ can function at least as the active ingredient.

The term "international units" or "IU" refers to is a unit of measurement for the amount of a substance; the mass or volume that constitutes one international unit varies based on which substance is being measured, and the variance is based on the biological activity or effect, for the purpose of easier comparison across substances. International units are used to quantify vitamins, hormones, some medications, vaccines, blood products, and similar biologically active substances. International units are used as a method of standardizing different forms of the same substance, thus, making them easier to compare in terms of their biological activity. For example, both vitamin D2 (ergocalciferol) and Vitamin D3 (cholecalciferol) are considered equivalent in terms of their biological activity. Thus, one international unit IU of vitamin D2 is equal to one international unit of vitamin D3.

The term "antioxidant" refers to a substance that inhibits oxidation. The antioxidant can optionally be an antimicrobial agent. Suitable antioxidants include, e.g., butylated hydroxytoluene (BHT), ascorbyl palmitate, vitamin E, and tocopheryl acetate (vitamin E acetate).

The term "sweetener" refers to a substance that provides a sweet taste. The sweetener can be natural or artificial. Suitable sweeteners include sugars (e.g., glucose, corn syrup, fructose, and sucrose) as well as sugar substitutes (e.g., honey, honey granules, aspartame, neotame, acesulfame potassium (Ace-K), saccharin, sodium saccharine, advantame, sucralose, monk fruit extract (mogrosides), stevia, rebaudioside A, sorbitol, xylitol, and lactitol).

The term "flavoring agent" or "flavorant" refers to a substance used to impart a flavor, e.g., to improve the attractiveness and acceptance by the patient. The basic taste sensations are salty, sweet, bitter, sour, and umami. Flavors may be chosen from natural and synthetic flavorings. An illustrative list of such agents includes volatile oils, synthetic flavor oils, flavoring aromatics, oils, liquids, oleoresins or extracts derived from plants, leaves, flowers, fruits, stems and combinations thereof. The flavoring agent can include, e.g., one or more of honey, anise, cherry, mint, peppermint, spearmint, menthol, levomenthol, watermint, gingermint, lemongrass, cardamom, sage, cinnamon, ginger, allspice, clove, eugenol, orange, wintergreen, lemon, lime, tangerine, ginger, mountain berry, mixed berry, and nutmeg. Suitable flavoring agents include, e.g., mountain berry and natural & artificial mixed berry.

The term "coloring agent" refers to a substance used to impart a color, e.g., to improve the appearance and attractiveness by the patient. Color consistency can be significant, as it allows easy identification of a medication to the patient. Furthermore, colors often improve the aesthetic look and feel of medications. By increasing these organoleptic properties, a patient is more likely to adhere to their schedule and therapeutic objectives will also have a better outcome for the patient. Suitable coloring agents include, e.g., FD&C Red #40.

The term "binder" or "gelling agent" refers to a substance that assists in holding or drawing other materials together to form a cohesive whole mechanically, chemically, by adhesion, or cohesion. This includes the use of a substance such as sodium carboxymethyl cellulose (Na CMC), carboxymethyl cellulose (CMC), sodium alginate, or a combination thereof, to effectively form an oral dissolvable film, by holding together the remaining substances (e.g., active ingredient, antioxidant, thickening agent, plasticizer, filler, and emulsifier) present in the oral dissolvable film.

The term "thickening agent" or "thickener" refers to a substance which can increase the viscosity of a liquid without substantially changing its other properties. Thickeners may also improve the suspension of other ingredients or emulsions which increases the stability of the oral dissolvable film. Suitable thickening agents include, e.g., hydroxypropyl methyl cellulose and polyvinylpyrrolidone.

The term "plasticizer" refers to a substance that, when added to polymer(s), make the polymer pliable and soft, enhancing the flexibility and plasticity of the films. They can be added to reduce the glass transition temperature of the polymer, improving the mechanical properties of the matrix. The plasticizer is believed to permeate the polymer structure, disrupting intermolecular hydrogen bonding, and permanently lowers intermolecular attractions. Plasticizers can be used to allow initial film forming, to reduce the brittleness, and improve the processability and flexibility of the resulting film, thereby avoiding cracking, e.g., during the curing process. Suitable plasticizers include, e.g., glycerin, polyethylene glycol, honey, propylene glycol, monoacetin, triacetin, triethyl citrate, sorbitol, 1,3-butanediol, D-glucono-1,5-lactone, diethylene glycol, castor oil, and combinations thereof.

The term "emulsion" refers to the suspension of one liquid in another liquid.

The term "emulsifier" refers to a substance that stabilizes an emulsion by increasing its kinetic stability. One class of emulsifiers is known as "surface active agents", or surfactants. Emulsifiers are compounds that typically have a polar or hydrophilic (i.e. water-soluble) part and a non-polar (i.e. hydrophobic or lipophilic) part. Because of this, emulsifiers tend to have more or less solubility either in water or in oil. Emulsifiers that are more soluble in water (and conversely, less soluble in oil) will generally form oil-in-water emulsions, while emulsifiers that are more soluble in oil will form water-in-oil emulsions. With the oral dissolvable films described herein, the emulsifier can include, e.g., at least one of polysorbate 80, polysorbate 20, polysorbate 60, hydroxylated lecithin, soy lecithin, sunflower lecithin, mono- and diglycerides, and ceteareth 20.

The term "solvent" refers to a substance that dissolves a solute, resulting in a solution. The solvent is typically a liquid and the quantity of solute that can dissolve in a specific volume of solvent typically varies with temperature. The term "solvent" includes water or ethanol (or a combination thereof), used to dissolve the substances present in the oral dissolvable film described herein (e.g., active ingredient, antioxidant, binder, thickening agent, plasticizer, and emulsifier), to effectively form a slurry.

The term "solubilizer" refers to a substance that increases the solubility of a solute in solvent and/or assists in maintaining the solubility of a solute in solvent. Suitable solubilizers include, e.g. cocoa butter (e.g., natural deodorized cocoa butter).

The term "filler" refers to a substance (e.g., bulking agent, such as microcrystalline cellulose or MCC) that can be added to a polymeric matrix or slurry, that can improve specific properties of the oral dissolvable film, such as physical properties, performance characteristics, or a combination thereof. As such, a suitable filler is microcrystalline cellulose (MCC).

The term "vitamin E" refers to a group of eight fat soluble compounds that include four tocopherols and four tocotrienols. Tocopherols are a class of organic chemical compounds, many of which have vitamin E activity. The vitamin E family comprise four tocotrienols (alpha, beta, gamma, delta) and four tocopherols (alpha, beta, gamma, delta). The critical chemical structural difference between tocotrienols and tocopherols is that tocotrienols have unsaturated isoprenoid side chains with three carbon-carbon double bonds versus saturated side chains for tocopherols.

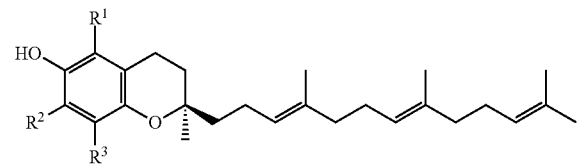

General chemical structure of tocotrienols, alpha (α)-Tocotrienol: $R^1$=Me, $R^2$=Me, $R^3$=Me; beta (β)-Tocotrienol: $R^1$=Me, $R^2$=H, $R^3$=Me; gamma (Τ)-Tocotrienol: $R^1$=H, $R^2$=Me, $R^3$=Me; delta (δ)-Tocotrienol: $R^1$=H, $R^2$=H, $R^3$=Me Vitamin E is fat soluble. As such, the term "vitamin E oil" refers to vitamin E suspended or dissolved in an oil carrier. When present in the oral dissolvable film described herein, the vitamin E can function at least as an antioxidant.

The molecules that contribute α-tocopherol activity are four tocopherols and four tocotrienols, within each group of four identified by the prefixes alpha-(α-), beta-(β-), gamma-(γ-), and delta-(δ-). For alpha (α)-tocopherol each of the three "R" sites has a methyl group ($CH_3$) attached. For beta (β)-tocopherol: $R^1$=methyl group, $R^2$=H, $R^3$=methyl group. For gamma (γ)-tocopherol: $R^1$=H, $R^2$=methyl group, $R^3$=methyl group. For delta(δ)-tocopherol: $R^1$=H, $R^2$=H, $R^3$=methyl group. The same configurations exist for the tocotrienols, except that the hydrophobic side chain has three carbon-carbon double bonds whereas the tocopherols have a saturated side chain.

The term "ascorbyl palmitate" refers to an ester formed from ascorbic acid and palmitic acid creating a fat-soluble form of vitamin C. Ascorbyl palmitate is also marketed as "vitamin C ester". The compound has the IUPAC name [(2S)-2-[(2R)-4,5-Dihydroxy-3-oxo-2-furyl]-2-hydroxyethyl] hexadecanoate; CAS No. 137-66-06; chemical formula $C_{22}H_{38}O_7$; and molar mass $C_{22}H_{38}O_7$. When present in the oral dissolvable film described herein, the ascorbyl palmitate can function at least as an antioxidant.

The term "sucralose" refers to an artificial sweetener and sugar substitute having the IUPAC name 1,6-dichloro-1,6-dideoxy-β-D-fructofuranosyl-4-chloro-4-deoxy-α-D-galactopyranoside; CAS No. 56038-12-02; chemical formula $C_{12}H_{19}Cl_3O_8$; and molar mass 397.64 g/mol. When present in the oral dissolvable film described herein, the sucralose can function at least as a sweetener.

The term "Nat & Art Mixed Berry" or "Natural & Artificial Mixed Berry" refers to a flavoring agent commercially available from Virginia Dare Extracts and Flavors (Brooklyn, N.Y.), with a Product No. BT03. When present in the oral dissolvable film described herein, the natural & artificial mixed berry can function at least as a flavoring agent.

The term "mountain berry" refers to a flavoring agent commercially available from MANE Flavor & Fragrance Manufacturer, Inc. (Milford, Ohio), with a Product No. F96522. When present in the oral dissolvable film described herein, the mountain berry can function at least as a flavoring agent.

The term "FD&C Red #40" refers to a red azo dye that goes by several names, including Allura Red AC and FD&C Red #40. It is used as a food dye and has the E number E129. It is usually supplied as its red sodium salt, but can also be used as the calcium and potassium salts. These salts are soluble in water. In solution, its maximum absorbance typically lies at about 504 nm. Allura Red AC has the preferred IUPAC name disodium 6-hydroxy-5-[(2-methoxy-5-methyl-4-sulfonatophenyl)diazenyl]naphthalene-2-sulfonate; CAS No. 25956-17-06; chemical formula $C_{18}H_{14}N_2Na_2O_8S_2$; and molar mass 496.42 g/mol. When present in the oral dissolvable film described herein, the FD&C Red #40 can function at least as a coloring agent.

The term "carboxymethyl cellulose," "CMC," "carboxymethylcellulose," or "carmellose" refers to a cellulose derivative with carboxymethyl groups ($-CH_2-COOH$) bound to some of the hydroxyl groups of the glucopyranose monomers that make up the cellulose backbone. It is often used as its sodium salt, sodium carboxymethyl cellulose (Na CMC). CMC has the CAS No. 9000-11-07 and structural formula below.

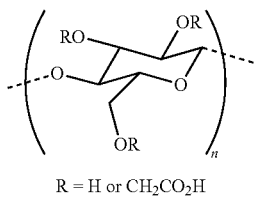

R = H or $CH_2CO_2H$

When present in the oral dissolvable film described herein, the sodium carboxymethyl cellulose can function at least as a binder.

The term "Kollidon 90 F" or "Kollidon® 90 F" refers to a soluble high-molecular povidone having a relatively high binding property within the povidone range. Kollidon® 90 F contains polyvinylpyrrolidone (PVP) and is commercially available from BASF (Ludwigshafen, DE or Florham Park, N.J., USA). When present in the oral dissolvable film described herein, the Kollidon® 90 F can function at least as a thickening agent.

The term "polyvinylpyrrolidone" or "PVP" refers to a water-soluble polymer made from the monomer N-vinylpyrrolidone. The compound has the IUPAC name 1-ethenylpyrrolidin-2-one; CAS. No. 9003-39-08; chemical formula $(C_6H_9NO)n$; and molar mass 2,500-2,500,000 g/mol. When present in the oral dissolvable film described herein, the polyvinylpyrrolidone (PVP) can function at least as a thickening agent.

The term "cocoa butter" (also called theobroma oil), refers to a pale-yellow, edible fat extracted from the cocoa bean. Cocoa butter is typically obtained from whole cocoa beans. Cocoa butter is sometimes deodorized to remove strong or undesirable tastes and odors. Cocoa butter contains a high proportion of saturated fats as well as monounsaturated oleic acid, which typically occurs in each triglyceride. The predominant triglycerides are POS, SOS, POP, where P=palmitic, O=oleic, and S=stearic acid residues. As such, the term "natural deodorized cocoa butter" refers to cocoa butter that is naturally derived (e.g., extracted from the cocoa bean) and is deodorized. When present in the oral dissolvable film described herein, the cocoa butter can function at least as a solubilizer.

The term "glycerin" (also called glycerine or glycerol) refers to a simple polyol compound having the preferred IUPAC name propane-1,2,3-triol; the CAS No. 56-81-5; chemical formula $C_3H_8O_3$; and molar mass 92.094 g/mol. When present in the oral dissolvable film described herein, the glycerin can function at least as a plasticizer.

The term "polysorbate 80" refers to a nonionic surfactant and emulsifier having the IUPAC name polyoxyethylene (20) sorbitan monooleate; CAS No. 9005-65-06; chemical formula $C_{64}H_{124}O_{26}$; and molar mass 1310 g/mol. This synthetic compound is a viscous, water-soluble yellow liquid. When present in the oral dissolvable film described herein, the polysorbate 80 can function at least as an emulsifier.

The term "microcrystalline cellulose" or "MCC" refers to refined wood pulp. MCC is a naturally occurring polymer, composed of glucose units connected by a 1-4 beta glycosidic bond. These linear cellulose chains are bundled together as microfibril spiraled together in plant cell walls. MCC is pure partially depolymerized cellulose synthesized from α-cellulose precursor. The MCC can be synthesized by different processes such as reactive extrusion, enzyme mediated, mechanical grinding, ultrasonication, steam explosion and acid hydrolysis. The later process can be done using mineral acids such as $H_2SO_4$, HCl and HBr as well as ionic liquids. The role of these reagents is to destroy the amorphous regions leaving the crystalline domains. The degree of polymerization is typically less than 400. When present in the oral dissolvable film described herein, the microcrystalline cellulose can function at least as a filler.

The term "Endurance™" or "Endurance MCC™" refers to a microcrystalline cellulose (CAS No. 9004-34-06) that is commercially available from FMC BioPolymer (Philadelphia, Pa.).

The term "thickness" refers to the measure of the least extended dimension of an object (e.g., oral dissolvable film). Thickness may be distinguished from length, which is vertical extent, and width, which is the distance from side to side, measuring across the object at right angles to the length.

The term "water content" or "moisture content" refers to the amount of water present in a substance (e.g., oral dissolvable film). The water can be present in the substance as bound water, unbound water, moisture, or a combination thereof.

The term "content uniformity" refers to an analysis parameter for the quality control of oral dissolvable films. Multiple oral dissolvable films are selected at random and a suitable analytical method is applied to assay the individual content of the substance (e.g., active ingredient) in oral dissolvable film. For example, in specific embodiments, the oral dissolvable film complies if not more than one (all within limits) individual content is outside the limits of 85 to 115% of the average content and none is outside the limits of 75 to 125% of the average content; and the oral dissolvable film fails to comply with the test if more than 3 individual contents are outside the limits of 85 to 115% of the average content or if one or more individual contents are outside the limits of 75% to 125% of the average content. See U.S. Pharmacopeia 29-NF24, Uniformity of Dosage Units <905> at page 2778.

The term "treating" (and equivalent terms such as "treat," "treated," and "treatment") of a subject includes the administration of an oral dissolvable film containing an active ingredient, to a subject with the purpose of preventing, curing, healing, alleviating, relieving, altering, remedying, ameliorating, improving, stabilizing or affecting a disease or disorder, or a symptom of a disease or disorder (e.g., to treat and/or prevent vitamin D deficiency and associated diseases, including rickets).

The term "subject" refers to living organisms such as humans, dogs, cats, and other mammals. Administration of the medicaments included in the oral films of the present invention can be carried out at dosages and for periods of time effective for the treatment of the subject. In some embodiments, the subject is a human. Unless otherwise specified, the human subject can be a male or female, and can further be an adult, adolescent, child, toddler, or infant.

The term "transmucosal" refers to any route of administration via a mucosal membrane or mucosal surface. Examples include, but are not limited to, buccal, sublingual, nasal, vaginal, and rectal.

The term "buccal administration" refers to a topical route of administration by which a drug held or applied in the buccal area (in the cheek) diffuses through the oral mucosa (tissues which line the mouth) and enters directly into the bloodstream. Buccal administration may provide better bioavailability of some drugs and a more rapid onset of action compared to oral administration because the medication does not pass through the digestive system and thereby avoids first pass metabolism.

The term "buccal space" (also termed the buccinator space) refers to a fascial space of the head and neck (sometimes also termed fascial tissue spaces or tissue spaces). It is a potential space in the cheek, and is paired on each side. The buccal space is superficial to the buccinator muscle and deep to the platysma muscle and the skin. The buccal space is part of the subcutaneous space, which is continuous from head to toe.

The term "oral mucosa" refers to the mucous membrane lining the inside of the mouth and consists of stratified squamous epithelium termed oral epithelium and an underlying connective tissue termed lamina propria. Oral mucosa can be divided into three main categories based on function and histology: (1) Masticatory mucosa, keratinized stratified squamous epithelium, found on the dorsum of the tongue, hard palate and attached gingiva; (2) Lining mucosa, nonkeratinized stratified squamous epithelium, found almost everywhere else in the oral cavity, including the: (a) Buccal mucosa refers to the inside lining of the cheeks and floor of the mouth and is part of the lining mucosa; (b) Labial mucosa refers to the inside lining of the lips and is part of the lining mucosa; and (c) Alveolar mucosa refers to the lining between the buccal and labial mucosae. It is a brighter red, smooth and shiny with many blood vessels, and is not connected to underlying tissue by rete pegs; and (3) Specialized mucosa, specifically in the regions of the taste buds on lingual papillae on the dorsal surface of the tongue that contains nerve endings for general sensory reception and taste perception.

The term "sublingual administration," from the Latin for "under the tongue," refers to the pharmacological route of administration by which substances diffuse into the blood through tissues under the tongue. When a drug comes in contact with the mucous membrane beneath the tongue, it is absorbed. Because the connective tissue beneath the epithelium contains a profusion of capillaries, the substance then diffuses into them and enters the venous circulation. In contrast, substances absorbed in the intestines are subject to first-pass metabolism in the liver before entering the general circulation. Sublingual administration has certain advantages over oral administration. Being more direct, it is often faster, and it ensures that the substance will risk degradation only by salivary enzymes before entering the bloodstream, whereas orally administered drugs must survive passage through the hostile environment of the gastrointestinal tract, which risks degrading them, by either stomach acid or bile, or by enzymes such as monoamine oxidase (MAO). Furthermore, after absorption from the gastrointestinal tract, such drugs must pass to the liver, where they may be extensively altered; this is known as the first pass effect of drug metabolism. Due to the digestive activity of the stomach and intestines, the oral route is unsuitable for certain substances.

The term "gingival administration" refers to the pharmacological route of administration by which substances diffuse into the blood through tissues in the gums. The gums or gingiva (plural: gingivae), consist of the mucosal tissue that lies over the mandible and maxilla inside the mouth.

The term "enteral administration" refers to a drug administration via the human gastrointestinal tract. Enteral administration involves the esophagus, stomach, and small and large intestines (i.e., the gastrointestinal tract). Methods of administration include oral and rectal. Enteral administration may be divided into three different categories, depending on the entrance point into the GI tract: oral (by mouth), gastric (through the stomach), and rectal (from the rectum). (Gastric introduction involves the use of a tube through the nasal passage (NG tube) or a tube in the belly leading directly to the stomach (PEG tube). Rectal administration usually involves rectal suppositories.) Enteral medications come in various forms, including, e.g., tablets to swallow, chew or dissolve in water; capsules and chewable capsules (with a coating that dissolves in the stomach or bowel to release the medication there), oral soluble films, time-release or sustained-release tablets and capsules (which release the medication gradually), osmotic delivery systems, powders or granules, and liquid medications or syrups.

The term "oral administration" refers to a route of administration where a substance (e.g., oral dissolvable film) is taken through the mouth. Many medications are taken orally because they are intended to have a systemic effect, reaching different parts of the body via the bloodstream.

The term "oral cavity" refers to the opening through which humans take in food and issue vocal sounds. The oral cavity is the first portion of the alimentary canal that receives food and produces saliva. The oral mucosa is the mucous membrane epithelium lining the inside of the mouth.

The term "pharmaceutically acceptable" refers to those compounds, excipients, active ingredients, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "dissolution" refers to a substance (e.g., oral dissolvable film) dissolving or being dissolved. When placed in the mouth, the substance will dissolve in saliva.

The term "disintegration" refers to a substance (e.g., oral dissolvable film) breaking up or falling apart. The substance will lose cohesion or strength and can fragment into pieces. When placed in the mouth, the substance will break apart in the saliva.

The term "organoleptic" or "organoleptic properties" refers to the aspects of an oral dosage form of a medication (e.g., oral dissolvable film) that create an individual experience via the senses-including taste, sight, smell, and touch.

Packaging of Oral Dissolvable Films

Packing considerations are important for storage, protection and stability of dosage forms. Packaging for oral dissolvable films typically includes foil paper or plastic pouches, single pouch, aluminum pouch, blister packaging with multiple units and barrier films. Barrier films are most commonly used for those drugs which are extremely moisture sensitive. In specific embodiments, the packaging will be child-resistant (e.g., child-resistant foil packages or child-resistant polyester/foil laminated pouches). Primary packaging made of a sealing pouch affords enough space for logos, codes, instructions, strengths, or other information. The films can be manufactured by a laminating process.

Desirably, a series of oral dissolvable films can be packaged together in accordance with the prescribed regimen or treatment, e.g., a 10-90 dosage supply, depending on the particular therapy. The individual films can be packaged on a backing and peeled off for use. Specifically, each film can be individually wrapped in a pouch or between foil and/or plastic laminate sheet. Alternatively, individual films can be packaged such that they are in direct contact with one another (e.g., they are stacked on top of one another). The use of a powder coating, for example, can decrease the likelihood that individual films will stick or adhere to one another. The multiple films that are packaged together can be located within a dispenser (e.g., cassette). Such a dispenser can contain a full supply of the medication typically prescribed for the intended therapy, but due to the thinness of the film and package, will likely be smaller and more convenient than traditional bottles used for tablets, capsules and liquids.

Administration of the Oral Dissolvable Film

Generally, the oral dissolvable film will be administered as indicated by the instructions and/or the prescribing medical practitioner. Preferably, the oral dissolvable film should not be applied to areas of the mouth with any open sores or lesions. The oral dissolvable film should also not be used if the package seal is broken or the oral film is cut or damaged. Preferably, with clean and dry hands, the oral dissolvable film is applied immediately after removal from the sealed package. The prescribing instructions may also indicate that the patient use the entire oral dissolvable film and should not cut or tear it.

Oral dissolving films that are designed to be applied on top of the tongue can effectively deliver the active ingredient via the enteral route. The patient will typically drink water to moisten the mouth. This may help the film stick and dissolve more easily. The orally dissolving film is then placed on top of the tongue where it dissolves and is swallowed, with or without water.

Buccal films provide for the transmucosal delivery of active ingredient. When the oral dissolvable film is a buccal film, the patient will typically place on the inside of the cheek and allow the film to dissolve. The entire buccal film can be held in place with clean, dry fingers for about 5 seconds and then left in place on the inside of the cheek until fully dissolved. Preferably, the buccal film should not be manipulated with the tongue or finger(s). The buccal film should adhere to the moist buccal mucosa and completely dissolve after application. Preferably, eating food or drink should also be avoided until the buccal film has dissolved. A buccal film, if chewed or swallowed, may result in lower peak plasma concentrations and lower bioavailability than when used as directed.

Alternatively, prior to administration the patient can wet the inside of the cheek or rinse the mouth with water to wet the area for placement of the buccal film. This may help the film stick and dissolve more easily. The buccal film can then be applied against the inside of the cheek.

When the oral dissolvable film is a sublingual film, the patient will typically place under the tongue and allow the film to dissolve. The sublingual film can then be applied under the tongue, close to the base, either to the left or the right of the center. The entire sublingual film can be held in place until fully dissolved. Preferably, the sublingual film should not be manipulated with the tongue or finger(s). The sublingual film should adhere to the moist sublingual mucosa and completely dissolve after application.

Alternatively, prior to administration the patient can drink water to moisten the mouth. This may help the film stick and dissolve more easily. Eating food or drink should also be avoided until the sublingual film has dissolved. A sublingual film, if chewed or swallowed, may result in lower peak plasma concentrations and lower bioavailability than when used as directed.

Dosages

The active ingredient(s) will preferably be present in the oral dissolvable film in a "therapeutically effective amount." The term "therapeutically effective amount" or "effective amount" means an amount of active ingredient, present in the oral dissolvable film, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

When an active ingredient is introduced to the oral dissolvable film, the amount of active ingredient per unit area is determined by the uniform distribution of the oral film. For example, because the oral dissolvable films exist as individual unit dosage forms, the amount of the active ingredient in the unit dosage form can be known with a great deal of accuracy. This is achieved because the amount of the active ingredient in a given area is substantially identical to the amount of active ingredient in an area of the same dimensions (i.e., length and width) in another part of the oral film. The accuracy in dosage is particularly advantageous when an accurate and precise amount of active ingredient is desirable.

The oral dissolvable films described herein are capable of accommodating a wide range of amounts of the active ingredient. The films are therefore capable of providing a relatively precise and accurate dosage amount (determined by the size of the film and concentration of the active in the slurry), regardless of whether the required dosage is high or low. For example, the oral dissolvable films described herein can include the active ingredient in up to about 10 mg/cm$^2$.

Specific Ranges, Values, and Embodiments

The specific embodiments describing the subject matter, ranges, and values provided below are for illustration purposes only, and do not otherwise limit the scope of the disclosed subject matter, as defined by the claims.

In specific embodiments, the oral dissolvable film that includes: (a) a polymeric matrix; (b) an active ingredient; (c) an antioxidant; and (d) optionally at least one of a sweetener, flavoring agent, and coloring agent.

In specific embodiments, the polymeric matrix includes: (a) a binder; (b) a thickening agent; (c) a plasticizer; and (d) an emulsifier.

In specific embodiments, the oral dissolvable film includes (a)-(d): (a) a polymeric matrix that includes (i)-(iv): (i) a binder; (ii) a thickening agent; (iii) a plasticizer; and (iv) an emulsifier; (b) an active ingredient; (c) an antioxidant; and (d) optionally at least one of a sweetener, flavoring agent, and coloring agent.

In specific embodiments, the oral dissolvable film includes (a)-(g): (a) a binder selected from the group consisting of carboxymethyl cellulose sodium, sodium alginate, and combinations thereof; (b) a thickening agent selected from the group consisting of polyvinylpyrrolidone, hydroxypropyl methyl cellulose, and combinations thereof; (c) a plasticizer that includes glycerin; (d) an emulsifier that includes polysorbate 80; (e) an active ingredient; (f) an antioxidant; and (g) optionally at least one of a sweetener, flavoring agent, and coloring agent.

In specific embodiments, the binder includes at least one of polyvinyl alcohol, sodium alginate, pullulan, methyl cellulose, hydroxypropyl cellulose, hydroxypropyl methyl cellulose, polyethylene glycols, carbopols, polycarbophils, carboxyvinyl copolymers, propylene glycol alginate, alginic acid, methyl methacrylate copolymers, tragacanth gum, guar gum, karaya gum, ethylene vinyl acetate, dimethylpolysiloxanes, polyoxyalkylene block copolymers, pectin, chitosan, carrageenan, xanthan gum, gellan gum, locust bean gum, hydroxyethylmethacrylate copolymers, and sodium carboxymethyl cellulose.

In specific embodiments, the binder includes at least one of carboxymethyl cellulose sodium, and sodium alginate.

In specific embodiments, the binder includes carboxymethyl cellulose sodium, present in the oral dissolvable film in 19.19±3 wt. %.

In specific embodiments, the thickening agent includes at least one of polyvinylpyrrolidone, and hydroxypropyl methyl cellulose.

In specific embodiments, the thickening agent includes Kollidon® 90 F (polyvinylpyrrolidone), present in the oral dissolvable film in 11.71±2 wt. %.

In specific embodiments, the plasticizer includes at least one of glycerin, sorbitol, mannitol, propylene glycol, and polyethylene glycol.

In specific embodiments, the plasticizer includes glycerin, present in the oral dissolvable film in 9.16±1.5 wt. %.

In specific embodiments, the emulsifier includes at least one of soy lecithin, sunflower lecithin, cetearyl alcohol, stearic acid, polysorbate 80, polysorbate 20, and polysorbate 60.

In specific embodiments, the emulsifier includes polysorbate 80, present in the oral dissolvable film in 7.32±1.5 wt. %.

In specific embodiments, the emulsifier includes polysorbate 80.

In specific embodiments, the active ingredient includes cholecalciferol (vitamin $D_3$).

In specific embodiments, the sole active ingredient is cholecalciferol (vitamin $D_3$).

In specific embodiments, the active ingredient includes cholecalciferol (vitamin $D_3$), present in the oral dissolvable film in 1.95±0.5 wt. %.

In specific embodiments, wherein the antioxidant includes at least one of tocopheryl acetate (vitamin E acetate), vitamin E, ascorbyl palmitate, and butylated hydroxytoluene (BHT), present in the oral dissolvable film in an aggregate amount of 9.25±1.5 wt. %.

In specific embodiments, the oral dissolvable film contains 4.53±1 wt. % cocoa butter as a solubilizer.

In specific embodiments, the oral dissolvable film contains 9.27±0.25 wt. % Endurance™ microcrystalline cellulose (MCC) as a filler.

In specific embodiments, the oral dissolvable film contains 2.33±0.25 wt. % sucralose as a sweetener.

In specific embodiments, the oral dissolvable film contains 10±0.1 wt. % mountain berry and 8±1 wt. % mixed berry, as a flavoring agent.

In specific embodiments, the oral dissolvable film includes a solvent.

In specific embodiments, the oral dissolvable film includes water as a solvent.

In specific embodiments, the oral dissolvable film contains 8.0±5 wt. % water as solvent.

In specific embodiments, the active ingredient, outside of the oral dissolvable film, exhibits instability to at least one of heat, light, moisture, and oxygen.

In specific embodiments, the active ingredient includes at least one of desmopressin (DDAVP) (D-amino D-arginine vasopressin); dronabinol ((−)-trans-Δ9-tetrahydrocannabinol); aspirin (acetylsalicylic acid); penicillin (PCN); dipyridamole; vorapaxar; procaine; atorvastatin; azithromycin; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; dopamine (3,4-dihydroxyphenethylamine); methyldopamine; naproxen; acetaminophen; erythromycin; bupropion; rifapentine; penicillamine; mexiletine; diltiazem; ibuprofen; cyclosporine; saquinavir; morphine; sertraline; cetirizine; N-[[2-methoxy-5-(1-methyl)phenyl]methyl]-2-(diphenylmethyl)-1-azabicylco[2.2.2]octan-3-amine; adrenaline; amiodarone hydrochloride; atropine sulphate; diazepam; ephedrine; frusemide; haloperidol; lignocaine; metoclopramide; noradrenaline; omeprazole; esomeprazole; ondansetron; phenytoin; vercuronium; acyclovir; amoxicillin; cefotetan; cefotaxime; metronidazole; cefuroxime; flucloxacillin; bupivacaine; cilazapril; amlodipine; felodipine; fesoterodine; isradipine; nifedipine; nimodipine; nisoldipine; itraconazole; ketoconazole, methylphenidate; fumarate; morphine; hydromorphone; promethazine; dopamine; epinephrine; norepinephrine; esterified estrogen; danofloxacin; methyldopate; cetirizine; vitamin A; vitamin B; vitamin C; vitamin D3 (cholecalciferol); L-cysteine; L-tryptophan; methyldopa; digoxin; nitroglycerin; aminophylline; amphotericin B; chlorpheniramine maleate; chlorpromazine HCl; cisplatin; dacarbazine; diazoxide; diphenhydramine; dopamine hydrochloride; doxycycline hyclate; droperidol; epinephrine hydrochloride; fluorouracil; folic acid; furosemide; hydrocortisone; isoproterenol; levarterenol bitartrate; menadiol sodium diphosphate; methadone; morphine sulphate; naloxone; neostigmine methylsulfate; nitroprusside solution; phenylephrine hydrochloride; phytonadione; prochlorperazine edisylate; propranolol hydrochloride; streptomycin sulphate; sulfisoxazole diolamine; terbutaline; testosterone cypionate; triflupromazine hydrochloride; vinblastine; vincristine sulphate; vitamin B complex; dextroamphetamine; ciprofloxacin; clarithromycin; griseofulvin; terbinafine; tetracycline hydrochloride; 1,4-dihydropyridines; 4-nerolidylcatechol; avobenzone; barnidipine; butyl methoxydibenzoylmethane; doxorubicin; fluoroquinolones; melatonin; naltrexone; cephalosporins; resveratrol; sericin; 3-hydroxyflavone; 4-methylbenzylidene camphor; 5-hydroxyflavones; antazoline; xylometazoline; nafazoline; ascorbic acid; carvedilol; cilnidipine; diclofenac; diflunisal; lansoprazole; manidipine; methotrexate; nicardipine; ofloxacin; oxolinic acid; phenylpropanoids; quercetin; ranitidine; rhein, sulfanilamide; triprolidine dexamethasone; dutasteride; doxercalciferol; calcitriol; tacrolimus; lorazepam; repaglinide; sirolimus; aprepitant; fenofibrate; paliperidone; aripiprazole lauroxil; progesterone; spironolactone; diosmin; celecoxib; halofantrine hydrochloride; ritonavir; meloxicam; nimesulide; danazol; glibenclamide; teniposide; propanidid; lopinavir; nabilone; etravirine; megestrol; nystatin; etomidate; flurbiprofen; propofol; clofazimine; paricalcitol; and tipranavir.

In specific embodiments, the active ingredient includes cholecalciferol (vitamin $D_3$).

In specific embodiments, the active ingredient includes cholecalciferol (vitamin $D_3$), present in the oral dissolvable film in up to 60K IU.

In specific embodiments, the active ingredient includes cholecalciferol (vitamin $D_3$), present in the oral dissolvable film in up to 50K IU.

In specific embodiments, the active ingredient includes cholecalciferol (vitamin $D_3$), present in the oral dissolvable film in up to 40K IU.

In specific embodiments, the active ingredient includes cholecalciferol (vitamin $D_3$), present in the oral dissolvable film in 50K±10K IU.

In specific embodiments, the active ingredient includes cholecalciferol (vitamin $D_3$), present in the oral dissolvable film in 40K±10K IU.

In specific embodiments, the antioxidant includes at least one of butylated hydroxytoluene (BHT), ascorbyl palmitate, vitamin E, and tocopheryl acetate (vitamin E acetate).

In specific embodiments, the sweetener includes at least one of acesulfame potassium, stevia, and sucralose.

In specific embodiments, the flavoring agent includes at least one of mountain berry and mixed berry.

In specific embodiments, the oral dissolvable film includes at least one of a solvent, a solubilizer, filler, and coloring agent.

In specific embodiments, the oral dissolvable film includes cocoa butter as a solubilizer.

In specific embodiments, the oral dissolvable film includes microcrystalline cellulose as filler.

In specific embodiments, the oral dissolvable film has a thickness of up to about 0.150 mm.

In specific embodiments, the oral dissolvable film has a thickness of up to about 0.140 mm.

In specific embodiments, the oral dissolvable film has a thickness of up to about 0.130 mm.

In specific embodiments, the oral dissolvable film has a thickness of about 0.130±0.004 mm.

In specific embodiments, the oral dissolvable film has a water content of about 8±5 wt. %.

In specific embodiments, the oral dissolvable film has a water content of about 8±4 wt. %.

In specific embodiments, the oral dissolvable film has a water content of about 8±3 wt. %.

In specific embodiments, the oral dissolvable film has a disintegration time of up to about 60 seconds upon application to a surface of the oral cavity.

In specific embodiments, the oral dissolvable film has a disintegration time of up to about 50 seconds upon application to a surface of the oral cavity.

In specific embodiments, the oral dissolvable film has a disintegration time of up to about 40 seconds upon application to a surface of the oral cavity.

In specific embodiments, the oral dissolvable film has a disintegration time of up to about 30 seconds upon application to a surface of the oral cavity.

In specific embodiments, the oral dissolvable film has a disintegration time of up to about 25 seconds upon application to a surface of the oral cavity.

In specific embodiments, the oral dissolvable film has a disintegration time of up to about 20 seconds upon application to a surface of the oral cavity.

In specific embodiments, the oral dissolvable film has a disintegration time of up to about 15 seconds upon application to a surface of the oral cavity.

In specific embodiments, the oral dissolvable film has a disintegration time of up to about 5-60 seconds upon application to a surface of the oral cavity.

In specific embodiments, the oral dissolvable film has a disintegration time of up to about 5-50 seconds upon application to a surface of the oral cavity.

In specific embodiments, the oral dissolvable film has a disintegration time of up to about 5-40 seconds upon application to a surface of the oral cavity.

In specific embodiments, the oral dissolvable film has a disintegration time of up to about 5-30 seconds upon application to a surface of the oral cavity.

In specific embodiments, the oral dissolvable film has a disintegration time of up to about 5-25 seconds upon application to a surface of the oral cavity.

In specific embodiments, the oral dissolvable film has a disintegration time of up to about 5-20 seconds upon application to a surface of the oral cavity.

In specific embodiments, the oral dissolvable film has a disintegration time of up to about 5-15 seconds upon application to a surface of the oral cavity.

In specific embodiments, the oral dissolvable film has a disintegration time of up to about 10-60 seconds upon application to a surface of the oral cavity.

In specific embodiments, the oral dissolvable film has a disintegration time of up to about 10-50 seconds upon application to a surface of the oral cavity.

In specific embodiments, the oral dissolvable film has a disintegration time of up to about 10-40 seconds upon application to a surface of the oral cavity.

In specific embodiments, the oral dissolvable film has a disintegration time of up to about 10-30 seconds upon application to a surface of the oral cavity.

In specific embodiments, the oral dissolvable film has a disintegration time of up to about 10-25 seconds upon application to a surface of the oral cavity.

In specific embodiments, the oral dissolvable film has a disintegration time of up to about 10-20 seconds upon application to a surface of the oral cavity.

In specific embodiments, the oral dissolvable film has a content uniformity such that the active ingredient ranges from about 90-110%, with the standard deviation of up to about 6%.

In specific embodiments, the oral dissolvable film has a content uniformity such that the active ingredient ranges from about 90-110%, with the standard deviation of up to about 5%.

In specific embodiments, the oral dissolvable film is configured to maintain the stability of the active ingredient, such that at 40° C. and 75% relative humidity, less than 35 wt. % of the active ingredient degrades over 6 months.

In specific embodiments, the oral dissolvable film is configured to maintain the stability of the active ingredient, such that at 40° C. and 75% relative humidity, less than 30 wt. % of the active ingredient degrades over 6 months.

In specific embodiments, the oral dissolvable film is configured to maintain the stability of the active ingredient during the shipment and storage at temperatures up to 25° C. and relative humidity up to 60%, whereby less than 15 wt. % of the active ingredient degrades over 6 months.

In specific embodiments, the oral dissolvable film is configured to maintain the stability of the active ingredient during the shipment and storage at temperatures up to 25° C. and relative humidity up to 60%, whereby less than 12.5 wt. % of the active ingredient degrades over 6 months.

In specific embodiments, the polymeric matrix is a flowable, water-soluble or water swellable film-forming matrix.

In specific embodiments, the polymeric matrix includes the active ingredient and antioxidant, such that the active ingredient and antioxidant are dispersed within the polymeric matrix.

In specific embodiments, the polymeric matrix includes at least one of a sweetener, flavoring agent, coloring agent, solvent, solubilizer, and filler, such that the at least one of the sweetener, flavoring agent, coloring agent, solvent, solubilizer, and filler are dispersed within the polymeric matrix.

In specific embodiments, the oral dissolvable film has a mass of up to 125 mg.

In specific embodiments, the oral dissolvable film has a mass of up to 100 mg.

In specific embodiments, the oral dissolvable film has a mass of 80±15 mg.

In specific embodiments, the oral dissolvable film has a mass of 80±5 mg.

In specific embodiments, oral dissolvable film that includes (a)-(j): (a) sodium carboxymethylcellulose; (b) Kollidon® 90 F (polyvinylpyrrolidone); (c) cocoa butter; (d) glycerin; (e) polysorbate 80; (f) Endurance™ microcrystalline cellulose; (g) at least one of tocopheryl acetate (vitamin E acetate), ascorbyl palmitate, and butylated hydroxytoluene (BHT); (h) cholecalciferol (vitamin $D_3$); (i) a flavoring agent; and (j) a sweetener.

In specific embodiments, oral dissolvable film that includes (a)-(k): (a) 19.19±3 wt. % sodium carboxymethyl cellulose; (b) 11.71±2 wt. % Kollidon® 90 F (polyvinylpyrrolidone); (c) 4.53±1 wt. % cocoa butter; (d) 9.16±1.5 wt. % glycerin; (e) 7.32±1 wt. % polysorbate 80; (f) 9.27±0.25 wt. % Endurance™ microcrystalline cellulose; (g) 9.25±1.25 wt. % of butylated hydroxytoluene (BHT), ascorbyl palmitate, tocopheryl acetate (vitamin E acetate), vitamin E, or a combination thereof; (h) 1.95±0.5 wt. % cholecalciferol (vitamin D3); (i) 17.27±2 wt. % flavoring agent; (j) 2.33±0.25 wt. % sweetener; and (k) 8.0±5 wt. % water.

In specific embodiments oral dissolvable film is formulated to contain the following:

| Ingredient | Amount (wt. %) in hydrous strip |
|---|---|
| Water (solvent) | 8.00 ± 3 wt. % |
| Sodium Carboxymethyl Cellulose (binder) | 19.19 ± 2 wt % |
| Kollidon ® 90 F PVP (thickening agent) | 11.71 ± 1 wt. % |
| Nat. Deodorized Cocoa Butter (solubilizer) | 4.53 ± 0.5 wt. % |
| Glycerin 99.7% USP (plasticizer) | 9.16 ± 1.5 wt. % |
| Polysorbate 80, NF (emulsifier') | 7.32 ± 1 wt. % |
| Mountain Berry (flavor) | 9.61 ± 1.5 wt. % |
| Sucralose USP/NF (sweetener) | 2.33 ± 0.5 wt. % |
| Endurance ™ Microcrystalline Cellulose (MCC) (tiller) | 9.27 ± 1.5 wt. % |
| Vitamin E Oil 1000 IU (antioxidant) | 9.20 ± 1.5 wt. % |
| Ascorbyl Palmitate (antioxidant) | 0.05 ± 0.01 wt. % |
| Vitamin D3 (active) | 1.95 ± 0.3 wt. % |
| Nat & Art Mixed Berry (flavor) | 7.66 ± 0.7 wt. % |
| FD&C Red #40 (coloring agent) | 0.01 ± 0.001 wt. % |
| Total | 100.00 wt. % |

In specific embodiments, oral dissolvable film is formulated to contain the following:

| Ingredient | Amount (wt. %) in hydrous strip |
|---|---|
| Water (solvent) | 8.00 wt. % |
| Sodium Carboxymethyl Cellulose (binder) | 19.19 wt. % |
| Kollidon ® 90 F PVP (thickening agent) | 11.71 wt. % |
| Nat. Deodorized Cocoa Butter (solubilizer) | 4.53 wt. % |
| Glycerin 99.7% USP (plasticizer) | 9.16 wt. % |
| Polysorbate 80, NF (emulsifier) | 7.32 wt. % |
| Mountain Berry (flavor) | 9.61 wt. % |
| Sucralose USP/NF (sweetener) | 2.33 wt. % |
| Endurance ™ Microcrystalline Cellulose (MCC) (filler) | 9.27 wt. % |
| Vitamin E Oil 1000 IU (antioxidant) | 9.20 wt. % |
| Ascorbyl Palmitate (antioxidant) | 0.05 wt. % |
| Vitamin D3 (active) | 1.95 wt. % |
| Nat & Art Mixed Berry (flavor) | 7.66 wt. % |
| FD&C Red #40 (coloring agent) | 0.01 wt. % |
| Total | 100.00 wt. % |

In specific embodiments, the method of orally administering the oral dissolvable film is a method of delivering an active ingredient to a subject in need thereof.

In specific embodiments, the method of orally administering the oral dissolvable film is a method of delivering cholecalciferol (vitamin $D_3$) to a subject in need thereof.

In specific embodiments, the administration occurs once daily.

In specific embodiments, the administration occurs once weekly.

In specific embodiments, the administration occurs once bi-weekly.

In specific embodiments, 1 oral dissolvable film is administered, per administration.

In specific embodiments, more than 1 oral dissolvable film is administered, per administration.

In specific embodiments, 2-3 oral dissolvable films are administered, per administration.

In specific embodiments, the oral dissolvable film includes cholecalciferol (vitamin $D_3$) and is administered to treat a subject afflicted with deficiency of vitamin D.

In specific embodiments, the oral dissolvable film includes cholecalciferol (vitamin $D_3$) and is administered to a subject at risk of deficiency of vitamin D.

In specific embodiments, the oral dissolvable film includes cholecalciferol (vitamin $D_3$) and is administered to a subject to prevent, treat, or a combination thereof, vitamin D deficiency.

In specific embodiments, the oral dissolvable film includes cholecalciferol (vitamin $D_3$) and is administered to a subject undergoing chemotherapy.

In specific embodiments, the oral dissolvable film includes cholecalciferol (vitamin $D_3$) and is administered to subject undergoing treatment for cancer.

In specific embodiments, the oral dissolvable film includes cholecalciferol (vitamin $D_3$) and is administered to prevent or reduce chemotherapy-induced myelosuppression in a subject being treated with a chemotherapeutic agent which induces myelosuppression.

In specific embodiments, the oral dissolvable film includes cholecalciferol (vitamin $D_3$) and is administered to a subject undergoing chemotherapy, wherein the chemotherapy involves the use of a cell cycle-specific chemotherapeutic agent.

In specific embodiments, the oral dissolvable film includes cholecalciferol (vitamin $D_3$) and is administered to a subject undergoing chemotherapy, wherein the chemotherapy involves the use of a nonspecific cell cycle chemotherapeutic agent.

In specific embodiments, the oral dissolvable film includes cholecalciferol (vitamin $D_3$) and is administered to a subject undergoing chemotherapy, wherein the chemotherapeutic agent is a cell cycle-specific agent in combination with a nonspecific cell cycle agent.

In specific embodiments, the oral dissolvable film includes cholecalciferol (vitamin $D_3$) and is administered to a subject undergoing chemotherapy, wherein the oral dissolvable film is administered prior to the administration of the chemotherapeutic agent.

In specific embodiments, the oral dissolvable film includes cholecalciferol (vitamin $D_3$) and is administered to a subject undergoing chemotherapy, wherein the oral dissolvable film is co-administered with the chemotherapeutic agent.

In specific embodiments, the oral dissolvable film includes cholecalciferol (vitamin $D_3$) and is administered to a subject undergoing chemotherapy, wherein the oral dissolvable film is administered subsequent to the administration of the chemotherapeutic agent.

In specific embodiments, the oral dissolvable film includes cholecalciferol (vitamin $D_3$) and is administered to a subject undergoing chemotherapy, wherein the oral dissolvable film is administered, both prior to and subsequent to, the administration of the chemotherapeutic agent.

In specific embodiments, the oral dissolvable film includes cholecalciferol (vitamin $D_3$) and is administered to a subject undergoing bone marrow transplant.

In specific embodiments, the oral dissolvable film includes cholecalciferol (vitamin $D_3$) and is administered to a subject undergoing bone marrow transplant, wherein the oral dissolvable film is administered prior to the bone marrow transplant.

In specific embodiments, the oral dissolvable film includes cholecalciferol (vitamin $D_3$) and is administered to a subject undergoing bone marrow transplant, wherein the oral dissolvable film is administered prior to the administration of an immunosuppressive agent.

In specific embodiments, the oral dissolvable film includes cholecalciferol (vitamin $D_3$) and is administered to a subject undergoing bone marrow transplant, wherein the oral dissolvable film is co-administered with an immunosuppressive agent.

In specific embodiments, the oral dissolvable film includes cholecalciferol (vitamin $D_3$) and is administered to a subject undergoing bone marrow transplant, wherein the oral dissolvable film is administered subsequent to the bone marrow transplant.

In specific embodiments, the oral dissolvable film includes cholecalciferol (vitamin $D_3$) and is administered to a subject undergoing bone marrow transplant, wherein the oral dissolvable film is administered, both prior to and subsequent to, the bone marrow transplant.

In specific embodiments, the oral dissolvable film includes cholecalciferol (vitamin $D_3$) and is administered to a subject undergoing bone marrow transplant, wherein the oral dissolvable film is administered subsequent to the administration of an immunosuppressive agent.

In specific embodiments, the oral dissolvable film includes cholecalciferol (vitamin $D_3$) and is administered to a subject undergoing bone marrow transplant, wherein the oral dissolvable film is administered, both prior to and subsequent to, the administration of an immunosuppressive agent.

In specific embodiments, the oral dissolvable film includes cholecalciferol (vitamin $D_3$) which upon oral administration is delivered orally.

In specific embodiments, the oral dissolvable film includes cholecalciferol (vitamin $D_3$) which, upon oral administration of the oral dissolvable film, is delivered enterally.

In specific embodiments, the oral dissolvable film includes cholecalciferol (vitamin $D_3$) which, upon oral administration of the oral dissolvable film, is delivered sublingually.

In specific embodiments, the oral dissolvable film includes cholecalciferol (vitamin $D_3$) which, upon oral administration of the oral dissolvable film, is delivered buccally.

In specific embodiments, the oral dissolvable film includes cholecalciferol (vitamin $D_3$) which, upon oral administration of the oral dissolvable film, is delivered transmucosal.

In specific embodiments, the oral dissolvable film is administered to a subject that is a human.

In specific embodiments, the oral dissolvable film is administered to a subject that is a human adult, at least 18 years old.

In specific embodiments, the oral dissolvable film is administered to a subject that is a human child, less than 18 years old.

Enumerated Embodiments

Specific enumerated embodiments <1> to <67> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<1> An oral dissolvable film that includes:
 (a) a polymeric matrix;
 (b) an active ingredient;
 (c) an antioxidant; and
 (d) optionally at least one of a sweetener, flavoring agent, and coloring agent.

<2> The oral dissolvable film of embodiment <1>, wherein the polymeric matrix includes:
  (a) a binder;
  (b) a thickening agent;
  (c) a plasticizer; and
  (d) an emulsifier.
<3> An oral dissolvable film that includes (a)-(d):
  (a) a polymeric matrix that includes (i)-iv):
    (i) a binder;
    (ii) a thickening agent;
    (iii) a plasticizer; and
    (iv) an emulsifier
  (b) an active ingredient;
  (c) an antioxidant; and
  (d) optionally at least one of a sweetener, flavoring agent, and coloring agent.
<4> The oral dissolvable film of any one of the above embodiments, wherein the binder includes at least one of polyvinyl alcohol, sodium alginate, pullulan, methyl cellulose, hydroxypropyl cellulose, hydroxypropyl methyl cellulose, polyethylene glycols, carbopols, polycarbophils, carboxyvinyl copolymers, propylene glycol alginate, alginic acid, methyl methacrylate copolymers, tragacanth gum, guar gum, karaya gum, ethylene vinyl acetate, dimethylpolysiloxanes, polyoxyalkylene block copolymers, pectin, chitosan, carrageenan, xanthan gum, gellan gum, locust bean gum, hydroxyethylmethacrylate copolymers, and sodium carboxymethyl cellulose.
<5> The oral dissolvable film of any one of the above embodiments, wherein the binder includes at least one of carboxymethyl cellulose sodium, and sodium alginate.
<6> The oral dissolvable film of any one of the above embodiments, wherein the binder includes carboxymethyl cellulose sodium, present in the oral dissolvable film in 19.19±3 wt. %.
<7> The oral dissolvable film of any one of the above embodiments, wherein the thickening agent includes at least one of polyvinylpyrrolidone, and hydroxypropyl methyl cellulose.
<8> The oral dissolvable film of any one of the above embodiments, wherein the thickening agent includes Kollidon 90 F (polyvinylpyrrolidone), present in the oral dissolvable film in 11.71±2 wt. %.
<9> The oral dissolvable film of any one of the above embodiments, wherein the plasticizer includes at least one of glycerin, sorbitol, mannitol, propylene glycol, and polyethylene glycol.
<10> The oral dissolvable film of anyone of the above embodiments, wherein the plasticizer includes glycerin, present in the oral dissolvable film in 9.16±1.5 wt. %.
<11> The oral dissolvable film of anyone of the above embodiments, wherein the emulsifier includes at least one of soy lecithin, sunflower lecithin, cetearyl alcohol, stearic acid, polysorbate 80, polysorbate 20, and polysorbate 60.
<12> The oral dissolvable film of anyone of the above embodiments, wherein the emulsifier includes polysorbate 80, present in the oral dissolvable film in 7.32±1.5 wt. %.
<13> The oral dissolvable film of anyone of the above embodiments, wherein the emulsifier includes polysorbate 80.
<14> The oral dissolvable film of anyone of the above embodiments, wherein the active ingredient includes cholecalciferol (vitamin $D_3$), present in the oral dissolvable film in 1.95±0.5 wt. %.
<15> The oral dissolvable film of anyone of the above embodiments, wherein the antioxidant includes at least one of tocopheryl acetate (vitamin E acetate), vitamin E, ascorbyl palmitate, and butylated hydroxytoluene (BHT), present in the oral dissolvable film in an aggregate amount of 9.25±1.5 wt. %.
<16> The oral dissolvable film of anyone of the above embodiments, containing 4.53±1 wt. % cocoa butter as a solubilizer.
<17> The oral dissolvable film of anyone of the above embodiments, containing 9.27±0.25 wt. % microcrystalline cellulose (MCC) as a filler.
<18> The oral dissolvable film of anyone of the above embodiments, containing 2.33±0.25 wt. % sucralose as a sweetener.
<19> The oral dissolvable film of anyone of the above embodiments, containing 9.61±1 wt. % mountain berry and 7.66±1 wt. % mixed berry, as a flavoring agent.
<20> The oral dissolvable film of any one of the above embodiments, containing water as solvent.
<21> The oral dissolvable film of any one of the above embodiments, containing 8.0±5 wt. % water as solvent.
0<22> An oral dissolvable film that includes (a)-(g):
  (a) a binder selected from the group consisting of carboxymethyl cellulose sodium, sodium alginate, and combinations thereof;
  (b) a thickening agent selected from the group consisting of polyvinylpyrrolidone, hydroxypropyl methyl cellulose, and combinations thereof;
  (c) a plasticizer that includes glycerin:
  (d) an emulsifier that includes polysorbate 80;
  (e) an active ingredient;
  (f) an antioxidant; and
  (g) optionally at least one of a sweetener, flavoring agent, and coloring agent.
<23> An oral dissolvable film that includes (a)-(k):
  (a) 19.19±3 wt. % sodium carboxymethyl cellulose;
  (b) 11.71±2 wt. % Kollidon 90 F (polyvinylpyrrolidone);
  (c) 4.53±1 wt. % cocoa butter;
  (d) 9.16±1.5 wt. % glycerin;
  (e) 7.32±1 wt. % polysorbate 80;
  (f) 9.27±0.25 wt. % microcrystalline cellulose;
  (g) 9.25±1.25 wt. % in the aggregate of butylated hydroxytoluene (BHT), ascorbyl Palmitate, vitamin E, tocopheryl acetate (vitamin E acetate), or a combination thereof;
  (h) 1.95±0.5 wt. % cholecalciferol (vitamin $D_3$);
  (i) 17.27±2 wt. % flavoring agent;
  (j) 2.33±0.25 wt. % sweetener; and
  (k) 8.0±5 wt. % water.
<24> The oral dissolvable film of any one of the above embodiments, wherein the active ingredient, outside of the oral dissolvable film, exhibits instability to at least one of heat, light, moisture, and oxygen.
<25> The oral dissolvable film of any one of the above embodiments, wherein the active ingredient includes at least one of desmopressin (DDAVP) (D-amino D-arginine vasopressin); dronabinol ((−)-trans-Δ9-tetrahydrocannabinol); aspirin (acetylsalicylic acid); penicillin (PCN); dipyridamole; vorapaxar; procaine; atorvastatin; azithromycin; pseudoephedrine; tiagabine; acitretin; rescinnamine; lovastatin; tretinoin; isotretinoin; simvastatin; ivermectin; verapamil; oxybutynin; hydroxyurea; selegiline; esterified estrogens; tranylcypromine; carbamazepine; ticlopidine; methyldopahydro; chlorothiazide; dopamine (3,4-dihydroxyphenethylamine); methyldopamine; naproxen; acetaminophen; erythromycin; bupropion; rifapentine; penicillamine; mexiletine; diltiazem; ibuprofen; cyclosporine; saquinavir; morphine; sertraline; cetirizine; N-[[2-methoxy-5-(I-methyl)phenyl]methyl]-2-(diphenylmethyl)-1-azabicylco[2.2.2]octan-3-amine; adrenaline; amiodarone hydrochloride; atropine sulphate; diazepam; ephedrine; frusemide; haloperidol; lignocaine; metoclopramide; noradrenaline; omeprazole; esomeprazole; ondansetron; phenytoin; vercuronium; acyclovir; amoxicillin; cefotetan; cefotaxime; metronidazole; cefuroxime; flucloxacillin; bupivacaine; cilazapril; amlodipine; felodipine; fesoterodine; isradipine; nifedipine; nimodipine; nisoldipine; itraconazole; ketoconazole, methylphenidate; fumarate; morphine; hydromorphone; promethazine; dopamine; epinephrine; norepinephrine; esterified estrogen; danofloxacin; methyldopate; cetirizine; vitamin A; vitamin B; vitamin C; vitamin D3 (cholecalciferol); L-cysteine; L-tryptophan; methyldopa; digoxin; nitroglycerin; aminophylline; amphotericin B; chlorpheniramine maleate; chlorpromazine HCl; cisplatin; dacarbazine; diazoxide; diphenhydramine; dopamine hydrochloride; doxycycline hyclate; droperidol; epinephrine hydrochloride; fluorouracil; folic acid; furosemide; hydrocortisone; isoproterenol; levarterenol bitartrate; menadiol sodium diphosphate; methadone; morphine sulphate; naloxone; neostigmine methylsulfate; nitroprusside solution; phenylephrine hydrochloride; phytonadione; prochlorperazine edisylate; propranolol hydrochloride; streptomycin sulphate; sulfisoxazole diolamine; terbutaline; testosterone cypionate; triflupromazine hydrochloride; vinblastine; vincristine sulphate; vitamin B complex; dextroamphetamine; ciprofloxacin; clarithromycin; griseofulvin; terbinafine; tetracycline hydrochloride; 1,4-dihydropyridines; 4-nerolidylcatechol; avobenzone; barnidipine; butyl methoxydibenzoylmethane; doxorubicin; fluoroquinolones; melatonin; naltrexone; cephalosporins; resveratrol; sericin; 3-hydroxyflavone; 4-methylbenzylidene camphor; 5-hydroxyflavones; antazoline; xylometazoline; nafazoline; ascorbic acid; carvedilol; cilnidipine; diclofenac; diflunisal; lansoprazole; manidipine; methotrexate; nicardipine; ofloxacin; oxolinic acid; phenylpropanoids; quercetin; ranitidine; rhein, sulfanilamide; triprolidine dexamethasone; dutasteride; doxercalciferol; calcitriol; tacrolimus; lorazepam; repaglinide; sirolimus; aprepitant; fenofibrate; paliperidone; aripiprazole lauroxil; progesterone; spironolactone; diosmin; celecoxib; halofantrine hydrochloride; ritonavir; meloxicam; nimesulide; danazol; glibenclamide; teniposide; propanidid; lopinavir; nabilone; etravirine; megestrol; nystatin; etomidate; flurbiprofen; propofol; clofazimine; paricalcitol; and tipranavir.

<26> The oral dissolvable film of any one of the above embodiments, wherein the active ingredient includes cholecalciferol (vitamin $D_3$).

<27> The oral dissolvable film of any one of the above embodiments, wherein the active ingredient includes cholecalciferol (vitamin $D_3$), present in 50K±10K IU.

<28> The oral dissolvable film of any one of the above embodiments, wherein the active ingredient includes cholecalciferol (vitamin $D_3$), present in 40K±10K IU.

<29> The oral dissolvable film of any one of the above embodiments, wherein the antioxidant includes at least one of butylated hydroxytoluene (BHT), ascorbyl palmitate, vitamin E, and tocopheryl acetate (vitamin E acetate).

<30> The oral dissolvable film of any one of the above embodiments, wherein the sweetener includes at least one of acesulfame potassium, stevia, and sucralose.

<31> The oral dissolvable film of anyone of the above embodiments, wherein the flavoring agent includes at least one of mountain berry and mixed berry.

<32> The oral dissolvable film of any one of the above embodiments, that includes at least one of a solvent, a solubilizer, filler, and coloring agent.

<33> The oral dissolvable film of any one of the above embodiments, that includes a solvent.

<34> The oral dissolvable film of any one of the above embodiments, that includes water as solvent.

<35> The oral dissolvable film of any one of the above embodiments, that includes cocoa butter as a solubilizer.

<36> The oral dissolvable film of any one of the above embodiments, that includes microcrystalline cellulose as filler.

<37> An oral dissolvable film that includes (a)-(j):
   (a) sodium carboxymethylcellulose;
   (b) Kollidon 90 F (polyvinylpyrrolidone);
   (c) cocoa butter;
   (d) glycerin;
   (e) polysorbate 80;
   (f) microcrystalline cellulose;
   (g) at least one of tocopheryl acetate (vitamin E acetate), vitamin E, ascorbyl palmitate, and butylated hydroxytoluene (BHT);
   (h) cholecalciferol (vitamin $D_3$);
   (i) a flavoring agent; and
   (j) a sweetener.

<38> The oral dissolvable film of any one of the above embodiments, having a thickness of about 0.130±0.004 mm.

<39> The oral dissolvable film of any one of the above embodiments, having a water content of about 8±5 wt. %.

<40> The oral dissolvable film of any one of the above embodiments, having a disintegration time of up to about 60 seconds upon application to a surface of the oral cavity.

<41> The oral dissolvable film of anyone of the above embodiments, having a content uniformity such that the active ingredient ranges from about 90-110%, with the standard deviation of up to about 6%.

<42> The oral dissolvable film of any one of the above embodiments, configured to maintain the stability of the active ingredient, such that at 40° C. and 75% relative humidity, less than 30 wt. % of the active ingredient degrades over 6 months.

<43> The oral dissolvable film of any one of the above embodiments, configured to maintain the stability of the active ingredient during the shipment and storage at temperatures up to 25° C. and relative humidity up to 60%, whereby less than 12.5 wt. % of the active ingredient degrades over 6 months.

<44> The oral dissolvable film of any one of the above embodiments, wherein the polymeric matrix is a flowable, water-soluble or water swellable film-forming matrix.

<45> The oral dissolvable film of any one of the above embodiments, wherein the polymeric matrix includes the active ingredient and antioxidant, such that the active ingredient and antioxidant are dispersed within the polymeric matrix.

<46> The oral dissolvable film of any one of the above embodiments, wherein the polymeric matrix includes at least one of a sweetener, flavoring agent, coloring agent, solvent, solubilizer, and filler, such that the at least one of the sweetener, flavoring agent, coloring agent, solvent, solubilizer, and filler are dispersed within the polymeric matrix.

<47> The oral dissolvable film of any one of the above embodiments, having a mass of up to 100 mg.

<48> The oral dissolvable film of any one of the above embodiments, having a mass of 80±15 mg.

<49> The oral dissolvable film of any one of the above embodiments, including:

| Ingredient | Amount (wt. %) in hydrous strip |
|---|---|
| Water (solvent) | 8.00 ± 3 wt. % |
| Sodium Carboxymethyl Cellulose (binder) | 19.19 ± 2 wt % |
| Polvvinylpyrrolidone (PVP) (thickening agent) | 11.71 ± 1 wt. % |
| Nat. Deodorized Cocoa Butter (solubilizer) | 4.53 ± 0.5 wt. % |
| Glycerin 99.7% USP (plasticizer) | 9.16 ± 1.5 wt. % |
| Polysorbate 80, NF (emulsifier) | 7.32 ± 1 wt. % |
| Mountain Berry (flavor) | 9.61 ± 1.5 wt. % |
| Sucralose USP/NF (sweetener) | 2.33 ± 0.5 wt. % |
| Microcrystalline Cellulose (MCC) (filler) | 9.27 ± 1.5 wt. % |
| Vitamin E Oil 1000 IU (antioxidant) | 9.20 ± 1.5 wt. % |
| Ascorbyl Palmitate (antioxidant) | 0.05 ± 0.01 wt. % |
| Vitamin D3 (active) | 1.95 ± 0.3 wt. % |
| Nat & Art Mixed Berry (flavor) | 7.66 ± 0.7 wt. % |
| FD&C Red #40 (coloring agent) | 0.01 ± 0.001 wt. % |
| Total | 100.00 wt. % |

<50> The oral dissolvable film of any one of the above embodiments, including:

| Ingredient | Amount (wt. %) in hydrous strip |
|---|---|
| Water (solvent) | 8.00 wt. % |
| Sodium Carboxymethyl Cellulose (binder) | 19.19 wt. % |
| Polvvinylpyrrolidone (PVP) (thickening agent) | 11.71 wt. % |
| Nat. Deodorized Cocoa Butter (solubilizer) | 4.53 wt. % |
| Glycerin 99.7% USP (plasticizer) | 9.16 wt. % |
| Polysorbate 80, NF (emulsifier) | 7.32 wt. % |
| Mountain Berry (flavor) | 9.61 wt. % |
| Sucralose USP/NF (sweetener) | 2.33 wt. % |
| Microcrystalline Cellulose (MCC) (filier) | 9.27 wt. % |
| Vitamin E Oil 1000 IU (antioxidant) | 9.20 wt. % |
| Ascorbyl Palmitate (antioxidant) | 0.05 wt. % |
| Vitamin D3 (active) | 1.95 wt. % |
| Nat & Art Mixed Berry (flavor) | 7.66 wt. % |
| FD&C Red #40 (coloring agent) | 0.01 wt. % |
| Total | 100.00 wt. % |

<51> A method of delivering an active ingredient to a subject in need thereof, the method includes orally administering to the subject an oral dissolvable film of any one of embodiments <1> to <50>.
<52> A method of delivering an active ingredient to a subject in need thereof, the method includes orally administering to the subject an oral dissolvable film of any one of embodiments <1> to <50>, wherein the active ingredient includes cholecalciferol (vitamin $D_3$), present in 50K±10K IU, and wherein the administration occurs once weekly.
<53> A method of delivering an active ingredient to a subject in need thereof, the method includes orally administering to the subject an oral dissolvable film of any one of embodiments <1> to <50>, wherein the active ingredient includes cholecalciferol (vitamin $D_3$), present in 40K±10K IU, and wherein the administration occurs once weekly.
<54> The method of anyone of embodiments <51> to <53>, wherein the active ingredient is cholecalciferol (vitamin $D_3$) and the subject is undergoing chemotherapy.
<55> The method of anyone of embodiments <51> to <53>, wherein the active ingredient is cholecalciferol (vitamin $D_3$) and the subject is being treated for cancer.
<56> The method of anyone of embodiments <51> to <53>, wherein the active ingredient is cholecalciferol (vitamin $D_3$) and the method includes preventing or reducing chemotherapy-induced myelosuppression in a subject being treated with a chemotherapeutic agent which induces myelosuppression.
<57> The method of anyone of embodiments <51> to <53>, wherein the active ingredient is cholecalciferol (vitamin $D_3$) and the method includes preventing, treating, or a combination thereof, of vitamin D deficiency.
<58> The method of anyone of embodiments <51> to <53>, wherein the active ingredient is delivered orally.
<59> The method of anyone of embodiments <51> to <53>, wherein the active ingredient is delivered enterally.
<60> The method of anyone of embodiments <51> to <53>, wherein the active ingredient is delivered sublingually.
<61> The method of anyone of embodiments <51> to <53>, wherein the active ingredient is delivered buccally.
<62> The method of anyone of embodiments <51> to <53>, wherein the active ingredient is delivered transmucosal.
<63> The method of anyone of embodiments <51> to <62>, wherein the subject is a human.
<64> The method of anyone of embodiments <51> to <62>, wherein the subject is a human adult, at least 18 years old.
<65> The method of anyone of embodiments <51> to <62>, wherein the subject is a human child, less than 18 years old.
<66> The method of any one of embodiments <51> to <65>, wherein 1 oral dissolvable film is administered once per week.
<67> The method of any one of embodiments <51> to <65>, wherein 2-3 oral dissolvable films are administered once per week.

The invention will be more fully understood by reference to the following examples. They should not, however, be construed as limiting the scope of the invention.

EXAMPLES

These examples serve to provide guidance to a skilled artisan to prepare the ODFs of the present invention, and methods of using the same. While particular embodiments of the present invention are described, the skilled artisan will appreciate that various changes and modifications can be made without departing from the spirit and scope of the inventions.

Example 1: Oral Dissolvable Film Containing Vitamin $D_3$

An oral dissolvable film containing Vitamin $D_3$ was formulated as described below.

| Ingredient | Amount (wt. %) in hydrous strip |
|---|---|
| Water (solvent) | 8.00 wt. % |
| Sodium Carboxymethyl Cellulose (binder) | 19.19 wt. % |
| Kollidon ®90 F PVP (Thickening Agent) | 11.71 wt. % |
| Nat. Deodorized Cocoa Butter (solubilizer) | 4.53 wt. % |
| Glycerin 99.7% USP (plasticizer) | 9.16 wt. % |
| Polysorbate 80, NF (emulsifier) | 7.32 wt. % |
| Mountain Berry (flavor) | 9.61 wt. % |
| Sucralose USP/NF (sweetener) | 2.33 wt. % |
| Endurance ™ Microcrystalline Cellulose (MCC) (filler) | 9.27 wt. % |
| Vitamin E Oil 1000 IU (antioxidant) | 9.20 wt. % |
| Ascorbyl Palmitate (antioxidant) | 0.05 wt. % |
| Vitamin D3 (active) | 1.95 wt. % |

-continued

| Ingredient | Amount (wt. %) in hydrous strip |
|---|---|
| Nat & Art Mixed Berry (flavor) | 7.66 wt. % |
| FD&C Red #40 (coloring agent) | 0.01 wt. % |
| Total | 100.00 wt. % |

Example 2: Vitamin D Manufacturing Process

The oral dissolvable film of Example 1 was manufactured as described below.
Blending Process
1. Weigh out every ingredient separately.
2. Heat the cocoa butter until it is fully melted.
3. Take 30% of the allotted water and place in a different container and heat to 100° F.
4. Heat the remaining water to 85° F.
5. In container A, place the cocoa butter, polysorbate 80, glycerin, Vitamin E, Vitamin D and ascorbyl palmitate.
6. Place the water of step 3 into container A and blend until the solution is homogenous, creating an emulsion (blending duration and rpm differ with different batch sizes). D3 crystal agglomerates must be at a minimum size/barely visible.
  a. Alternative step to be carried out for active ingredient stability: Using a water bath, heat the emulsion to 118-122° F. and blend until vitamin D3 crystalline material are completely in solution.
7. In container B, place the sucralose, mountain berry flavor, mixed berry flavor, microcrystalline cellulose and the red 40 coloring.
8. Add the remaining water from step 4 into container B and blend thoroughly until the solution is homogenous (blending duration and rpm differ with different batch sizes).
9. Add emulsion of container A into container B and blend thoroughly until homogenous.
10. Slowly add the Kollidon PVP and blend thoroughly until homogenous.
11. Slowly add the Cekol 30 (carboxymethyl cellulose) and blend thoroughly until homogenous.
12. Allow the slurry to cool to 80° F. before the curing process.
Curing Process
13. Keep slurry between 75-80° F.
14. Heat the oven to 180° F.
15. Set the extruding pin gauge to 700 μm
16. Run the slurry on siliconized paper through the oven.
17. Cure the slurry for about 6-8 minutes, or when cured film product is about 8% moisture (between 7.5-10%)
18. Cut the film product to 80 mg units.

Example 3: Characterization and Evaluation

The oral dissolvable film of Example 1 was evaluated to determine whether it possesses the desired aesthetic and performance characteristics, as well as any desired mechanical properties.

Example 3a: In Vivo Evaluation (i.) Organoleptic Evaluation

An in vivo test of sample ODF was carried out on a population of six (6) healthy human volunteers. Each volunteer received a sample ODF, was asked to place it in their oral cavity (e.g., on the tongue, under the tongue, or against the cheek), and to rate the taste of the ODF. Once the ODF was administered, the participants were not permitted to drink or eat until the ODF was completely dissolved. The volunteers were asked to rate the taste of the ODF from either very bad taste, bad taste, medium taste, good taste, and very good taste. The results are provided in the table below.

| | Organoleptic Evaluation | | |
|---|---|---|---|
| Volunteer | Under the tongue (sublingual) | Against the cheek (buccal) | On top of the tongue |
| 1 | Taste good | | |
| 2 | Taste very good | | |
| 3 | | Taste very good | |
| 4 | | Taste good | |
| 5 | Taste very good | | |
| 6 | | | Taste very good |

(ii.) Qualitative Assessment

An in vivo test of sample ODF was carried out on a population of five (5) healthy human volunteers. Each volunteer received a sample ODF, was asked to place it in their oral cavity, on the tongue. The volunteers were then asked to rate the qualitative assessment of the ODF. Once the ODF was administered, the participants were not permitted to drink or eat until the ODF was completely dissolved. The results are provided below.
1. 2 (40%) reported that the film stayed on the tongue and 1 (20%) reported that the film adhered to the palate
2. 0 (0%) reported feeling discomfort or pain
3. 2 (40%) reported feeling slight numbness or loss of sensation in their mouth
4. 0 (0%) reported feeling irritation
5. 5 (100%) reported that the taste was either good or very good
6. 0 (0%) reported experience of excessive salivation
7. 5 (100%) rated the experience pleasant to very pleasant (iii.) Oral Disintegration: Disintegration Test Method 18-9-22-Z An in vivo test of sample ODF was carried out on a population of six (6) healthy human volunteers. Each volunteer received a sample ODF. Each volunteer was asked to place a sample ODF in their oral cavity (e.g., on the tongue, under the tongue, or against the cheek) and to indicate when the ODF completely disintegrated. The time for disintegration was measured by using a stopwatch. The participants were instructed what they could or could not do while measuring the time to mimic as close as possible the intended intake by the target subject (e.g., buccal ODF should not be interrupted with tongue movement). Immediately after the film disintegrated completely, the stopwatch was stopped, and the time recorded. The results are provided in the table below.

| | Oral Disintegration | | |
|---|---|---|---|
| Volunteer | Under the tongue (sublingual) | Against the cheek buccal | On top of the tongue |
| 1 | 17 sec | | |
| 2 | 19 sec | | |
| 3 | | 15 sec | |
| 4 | | 14 sec | |
| 5 | 18 sec | | |
| 6 | | | 12 sec |

Example 3b: In Vitro Evaluation

The in vitro evaluations below were obtained from sample ODFs.

| | Average In vitro Disintegration | Average pH | Average tensile strength |
|---|---|---|---|
| Sample ODFs | 14.6 ± 2.5 seconds | 7.0 ± 0.1 | 16.5 ± 1.9 Newtons |

The invention claimed is:

1. A method of delivering cholecalciferol (vitamin $D_3$) to a human subject in need thereof, the method comprising orally administering to the human subject an oral dissolvable film comprising:
   (i) water;
   (ii) sodium carboxymethyl cellulose (Na CMC);
   (iii) polyvinylpyrrolidone (PVP);
   (iv) natural deodorized cocoa butter, present in 4.53±0.5 wt. % of the oral dissolvable film;
   (v) glycerin;
   (vi) polysorbate 80;
   (vii) microcrystalline cellulose (MCC);
   (viii) vitamin E;
   (ix) a.scorbyl palmitate;
   (x) vitamin $D_3$;
   (xi) optionally flavoring agent;
   (xii) optionally sweetener; and
   (xiii) optionally coloring agent, wherein one oral dissolvable film is administered to the subject once per week.

2. The method of claim 1, wherein upon orally administering to the human subject the oral dissolvable film, the cholecalciferol (vitamin $D_3$) is delivered enterally.

3. The method of claim 1, wherein the oral dissolvable film is administered to the subject to prevent vitamin D deficiency, to treat vitamin D deficiency, or a combination thereof.

4. The method of claim 1, wherein the oral dissolvable film comprises the water as a solvent, and is present in 8.00±3 wt. % of the oral dissolvable film.

5. The method of claim 1, wherein the oral dissolvable film comprises the sodium carboxymethyl cellulose as a binder, and is present in 19.19±2 wt. % of the oral dissolvable film.

6. The method of claim 1, wherein the oral dissolvable film comprises the polyvinylpyrrolidone, as a thickening agent, and is present in 11.71±1 wt. % of the oral dissolvable film.

7. The method of claim 1, wherein the oral dissolvable film comprises the glycerin as a plasticizer, and is present in 9.16±1.5 wt. % of the oral dissolvable film.

8. The method of claim 1, wherein the oral dissolvable film comprises the polysorbate 80 as an emulsifier, and is present in 7.32±1 wt. % of the oral dissolvable film.

9. The method of claim 1, wherein the oral dissolvable film comprises the microcrystalline cellulose (MCC) as a filler, and is present in 9.27±1.5 wt. % of the oral dissolvable film.

10. The method of claim 1, wherein the oral dissolvable film comprises the vitamin E as an antioxidant, and is present as vitamin E oil in 9.20±1.5 wt. % of the oral dissolvable film.

11. The method of claim 1, wherein the oral dissolvable film comprises the ascorbyl palmitate as an antioxidant, and is present in 0.05±0.01 wt. % of the oral dissolvable film.

12. The method of claim 1, wherein the oral dissolvable film comprises vitamin $D_3$ in an amount of 1.95±0.3 wt. % of the oral dissolvable film.

13. The method of claim 1, wherein the oral dissolvable film comprises vitamin $D_3$ in an amount of 50K±10K IU.

14. The method of claim 1, wherein the oral dissolvable film comprises vitamin $D_3$ in an amount of 40K±10K IU.

15. The method of claim 1, wherein the oral dissolvable film comprises at least one of mountain berry and natural & artificial mixed berry as a flavoring agent, and is present in an aggregate amount of 17.27±2.2 wt. % of the oral dissolvable film.

16. The method of claim 1, wherein the oral dissolvable film comprises sucralose as a sweetener, and is present in 2.33±0.5 wt. % of the oral dissolvable film.

17. The method of claim 1, wherein the oral dissolvable film comprises FD&C Red #40 as a coloring agent, and is present in 0.01±0.001 wt. % of the oral dissolvable film.

18. The method of claim 1, wherein the oral dissolvable film comprises

| Ingredient | Amount (wt. %) in hydrous strip |
|---|---|
| Water | 8.00 ± 3 wt. % |
| Sodium Carboxymethyl Cellulose (Na CMC) | 19.19 ± 2 wt. % |
| Polyvinylpyrrolidone (PVP) | 11.71 ± 1 wt. % |
| Natural Deodorized Cocoa Butter | 4.53 ± 0.5 wt. % |
| Glycerin (99.7% USP) | 9.16 ± 1.5 wt. % |
| Polysorbate 80, NF | 7.32 ± 1 wt. % |
| Mountain Berry | 9.61 ± 1.5 wt. % |
| Sucralose USP/NF | 2.33 ± 0.5 wt. % |
| Microcrystalline Cellulose (MCC) | 9.27 ± 1.5 wt. % |
| Vitamin E Oil 1000 IU | 9.20 ± 1.5 wt. % |
| Ascorbyl Palmitate | 0.05 ± 0.01 wt. % |
| Vitamin $D_3$ | 1.95 ± 0.3 wt. % |
| Natural & Artificial Mixed Berry | 7.66 ± 0.7 wt. % |
| FD&C Red #40 | 0.01 ± 0.001 wt. % |
| Total | 100.00 wt. %. |

19. The method of claim 1, wherein the oral dissolvable film comprises

| Ingredient | Amount (wt. %) in hydrous strip |
|---|---|
| Water | 8.00 wt. % |
| Sodium Carboxymethyl Cellulose (Na CMC) | 19.19 wt. % |
| Polyvinylpyrrolidone (PVP) | 11.71 wt. % |
| Natural Deodorized Cocoa Butter | 4.53 wt. % |
| Glycerin (99.7% USP) | 9.16 wt. % |
| Polysorbate 80, NF | 7.32 wt. % |
| Mountain Berry | 9.61 wt. % |
| Sucralose USP/NF | 2.33 wt. % |
| Microcrystalline Cellulose (MCC) | 9.27 wt. % |
| Vitamin E Oil 1000 IU | 9.20 wt. % |
| Ascorbyl Palmitate | 0.05 wt. % |
| Vitamin $D_3$ | 1.95 wt. % |
| Natural & Artificial Mixed Berry | 7.66 wt. % |
| FD&C Red #40 | 0.01 wt. % |
| Total | 100.00 wt. %. |

20. The method of claim 1, wherein the oral dissolvable film has a thickness of 0.130±0.004 mm.

21. The method of claim 1, wherein the oral dissolvable film has a water content of 8±5 wt. %.

22. The method of claim 1, wherein the oral dissolvable film has a. disintegration time of 5 to 40 seconds, upon application to a surface of the oral cavity.

23. The method of claim 1, wherein the oral dissolvable film has a content uniformity such that the vitamin $D_3$ ranges from about 90-110%, with the standard deviation of up to about 6%.

24. The method of claim 1, wherein the oral dissolvable film has a mass of 80±15 mg.

25. The method of claim 1, wherein the oral dissolvable film is administered to a subject: (i) afflicted with deficiency of vitamin D; (ii) at risk of deficiency of vitamin D; (iii) undergoing chemotherapy; (iv) undergoing treatment for cancer; (v) undergoing bone marrow transplant; or any combination thereof.

26. The method of claim 1, wherein the oral dissolvable film comprises:
   (i) water;
   (ii) sodium carboxymethyl cellulose (Na CMC);
   (iii) polyvinylpyrrolidone (PVP);
   (iv) natural deodorized cocoa butter, present in 4.53±0.5 wt. % of the oral dissolvable film;
   (v) glycerin;
   (vi) polysorbate 80;
   (vii) microcrystalline cellulose (MCC);
   (viii) vitamin E;
   (ix) ascorbyl palmitate;
   (x) vitamin $D_3$;
   (xi) flavoring agent;
   (xii) sweetener; and
   (xiii) coloring agent.

\* \* \* \* \*